(12) United States Patent
Noguera et al.

(10) Patent No.: US 10,144,938 B2
(45) Date of Patent: Dec. 4, 2018

(54) METHODS OF PROCESSING AROMATIC COMPOUNDS

(71) Applicant: WISCONSIN ALUMNI RESEARCH FOUNDATION, Madison, WI (US)

(72) Inventors: Daniel R. Noguera, Madison, WI (US); Timothy J. Donohue, Middleton, WI (US); Julian Z. Oshlag, Madison, WI (US); Weiping Zhang, Madison, WI (US); Samantha L. Austin, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 412 days.

(21) Appl. No.: 15/136,433

(22) Filed: Apr. 22, 2016

(65) Prior Publication Data

US 2016/0312257 A1    Oct. 27, 2016

Related U.S. Application Data

(60) Provisional application No. 62/152,135, filed on Apr. 24, 2015.

(51) Int. Cl.
| | |
|---|---|
| *C12P 19/02* | (2006.01) |
| *C12P 7/40* | (2006.01) |
| *C12P 7/10* | (2006.01) |
| *C12N 9/00* | (2006.01) |
| *C12N 9/02* | (2006.01) |
| *C12P 7/14* | (2006.01) |

(52) U.S. Cl.
CPC .............. *C12P 19/02* (2013.01); *C12N 9/001* (2013.01); *C12N 9/93* (2013.01); *C12P 7/10* (2013.01); *C12P 7/14* (2013.01); *C12P 7/40* (2013.01); *Y02E 50/16* (2013.01); *Y02E 50/343* (2013.01)

(58) Field of Classification Search
None
See application file for complete search history.

(56) References Cited

PUBLICATIONS

Austin, S. Utilization of corn stover hydrolysates by Rhodobacter sphaeroides and Rhodopseudomonas palustris under photoheterotrophic conditions. MS Thesis, University of Wisconsin, Madison, 2013.
Reknes, K. et al., Effect of modifications of lignosulfonate on adsorption on cement and fresh concrete properties. Sixth CANMET/ACI International Conference on Superplasticizers and Other Chemical Admixtures in Concrete, SP-195, American Concrete Institute, Farmington Hills, MI, 2000, pp. 127-142.
Alonso, M.V. et al., Modification of ammonium lignosulfonate by phenolation for use in phenolic resins. *Bioresour. Technol.*, 2005, 96, 1013-1018 (Abstract).
Anders, H.J. et al., Taxonomic position of aromatic-degrading denitrifying pseudomonad strains K 172 and KB 740 and their description as new members of the genera Thauera, as *Thauera aromatica* sp. nov., and Azoarcus, as *Azoarcus evansii* sp. nov., respectively, members of the beta subclass of the Proteobacteria. Int J Syst Bacteriol. Apr. 1995;45(2):327-33.
Auburger, G. et al., Activation and degradation of benzoate, 3-phenylpropionate and crotonate by Syntrophus buswellii strain GA. Evidence for electron-transport phosphorylation during crotonate respiration. Appl Microbiol Biotechnol. Feb. 1996;44(6):807-15.
Austin, S. Metabolism of Multiple Aromatic Compounds in Corn Stover Hydrolysate by Rhodopseudomonas palustris. Environmental Science & Technology (vol. 49) 8914-8922, 2015.
Bak, F. et al., Anaerobic degradation of phenol and phenol derivatives by *Desulfobacterium phenolicum* gen. nov., sp. nov. Arch. Microbiol. 1986 146:177-180.
Barbosa, M. J. et al., Acetate as a carbon source for hydrogen production by photosynthetic bacteria. J. Biotechnol. 2001, 85, (1), 25-33.
Beller, H.R. et al., Isolation and characterization of a novel toluene-degrading, sulfate-reducing bacterium. Appl Environ Microhiol. Apr. 1996;62(4):1188-96.
Bellissimi, E. et al., Effects of acetic acid on the kinetics of xylose fermentation by an engineered, xylose-isomerase-based *Saccharomyces cerevisiae* strain. FEMS Yeast Res. 2009, 9, (3), 358-364.
Blake, C.K. et al., Plasmid pCBI carries genes fron anaerobic benzoate catabolism in *Alcaligenes xylosoxidans* subsp. denitrificans PN-1. J Bacteriol. Nov. 1987;169(11):4878-83.
Breese, K. et al., Genes coding for benzoyl-CoA pathway of anaerobic aromatic metabolism in the bacterium Tauera aromatica. Eur J Biochem. Aug. 15, 1998;256(1):148-54.
Chambel, A. et al., Effect of cinnamic acid on the growth and on plasma membrane H+-ATPase activity of *Saccharomyces cerevisiae*. Int. J. Food Microbial. 1999, 50, (3), 173-179.
Chundawat, S.P.S. et al., Multifaceted characterization of cell wall decomposition products formed during ammonia fiber expansion (AFEX) and dilute acid based pretreatments. Bioresour. Technol., 2010, 101, 8429-8438.
Chundawat, S.P.S. et al., Multi-scale visualization and characterization of lignocellulosic plant cell wall deconstruction during thermochemical pretreatment. Energy Environ. Sci., 2011, 4, 973-984.

(Continued)

*Primary Examiner* — Manjunath N Rao
*Assistant Examiner* — Jae W Lee
(74) *Attorney, Agent, or Firm* — Daniel A. Blasiole; DeWitt Ross & Stevens S.C.

(57) ABSTRACT

A method of processing a solution comprising aromatic compounds. The method includes culturing a first microorganism in the solution for a time sufficient to reduce an amount of an aromatic compound and thereby generate a processed solution. The culturing may remove an aromatic compound deleterious to growth of a second microorganism without substantially reducing fermentable sugars, thereby permitting enhanced growth of the second microorganism in the processed solution. The culturing may additionally or alternatively convert an aromatic compound into a commodity chemical. The methods of the present invention are advantageous for processing lignocellulosic biomass for upgrading to biofuel or for generating commodity chemicals therefrom.

22 Claims, 10 Drawing Sheets

Specification includes a Sequence Listing.

(56) References Cited

PUBLICATIONS da Costa Sousa, L. et al., Next-Generation Ammonia Pretreatment Enhances Cellulosic Biofuel Production. Energy Environ. Sci., 2016, 9, 1215-1223.

Delgenes, J. P. et al., Effects of lignocellulose degradation products on ethanol fermentations of glucose and xylose by *Saccharomyces cerevisiae, Zymomonas mobilis, Pichia stipitis,* and *Candida shehatae.* Enzyme Microb. Technol. 1996, 19, (3), 220225.

Dutton, P. L. et al., The Metabolism of Aromatic Compounds by Rhodopseudomonas palustris. Biochem. J. 1969, 113, 525.

Egland, P. G. et al., A cluster of bacterial genes for anaerobic benzene ring biodegradation. Proc. Natl. Acad. Sci. USA 1997, 94, (12), 6484-6489.

Fitzgerald, D. J. et al., Mode of antimicrobial action of vanillin against *Escherichia coli, Lacto bacillus plantarum* and *Listeria innocua.* J. Appl. Microbiol. 2004, 97, (1), 104-113.

Gall, D. L. et al., Benzoyl coenzyme A pathway-mediated metabolism of meta-hydroxy-aromatic acids in Rhodopseudomonas palustris. J Bacteriol 2013, 195, (18), 4112-20.

Gibson, J. et al., 4-hydroxybenzoyl coenzyme A reductase (dehydroxylating) is required for anaerobic degradation of 4-hydroxybenzoate by Rhodopseudomonas palustris and shares features with molybdenum-containing hydroxylases. J. Bacteriol. 1997, 179, (3), 634-642.

Gorny, N. et al., Anaerobic degradation of catechol by *Desulfobacterium* sp. strain Cat2 proceeds via carboxylationto protocatechuate. Appl Environ Microbiol. Sep. 1994;60(9):3396-400.

Harrison, F. H. et al., The pimFABCDE operon from Rhodopseudomonas palustris mediates dicarboxylic acid degradation and participates in anaerobic benzoate degradation. Microbiology—Sgm 2005, 151, 727-736.

Harwood, C. S. et al., Anaerobic and aerobic metabolism of diverse aromatic compounds by the photosynthetic bacterium Rhodopseudomonas palustris. Appl. Environ. Microbiol. 1988, 54, (3), 712-717.

Harwood, C. S. et al., Anaerobic metabolism of aromatic compounds via the benzoyl-CoA pathway. FEMS Microbiol. Rev. 1998, 22, (5), 439-458.

Hirakawa, H. et al., Anaerobic p-Coumarate Degradation by Rhodopseudomonas palustris and Indentification of CouR, a MarR Repressor Protein That Binds p-Coumaroyl Coenzyme A. J. Bacteriol. 2012, 194, (8), 1960-1967

Hopkins, B.T. et al., Evidence for anaerobic syntrophic benzoate degradation threshold and isolation of the syntrophic benzoate degrader. Appl Environ Microbiol. Feb. 1995;61(2):526-30.

Humpula, J. F. et al., Rapid quantification of major reaction products formed during thermochemical pretreatment of lignocellulosic biomass using GC-MS. Journal of Chromatography B—Analytical Technologies in the Biomedical and Life Sciences 2011, 879, (13-14), 1018-1022.

Iwaki, A. et al., Vanillin Inhibits Translation and Induces Messenger Ribonucleoprotein (mRNP) Granule Formation in *Saccharomyces cerevisiae*: Application and Validation of High-Content, Image-Based Profiling. Plos One 2013, 8, (4).

Jonsson, L. J. et al., Detoxification of wood hydrolysates with laccase and peroxidase from the white-rot fungus Trametes versicolor. Appl. Microbiol. Biotechnol. 1998, 49, (6), 691-697.

Keating, D. H. et al., Aromatic inhibitors derived from ammonia-pretreated lignocellulose hinder bacterial ethanologenesis by activating regulatory circuits controlling inhibitor efflux and detoxification. Frontiers in Microbiology 2014, 5.

Kim, M. K. et al., Regulation of benzoate-CoA ligase in Rhodopseudomonas palustris. FEMS Microbiol. Lett. 1991, 83, (2), 199-203.

Kim, D. H. et al., Continuous cultivation of photosynthetic bacteria for fatty acid production. Bioresour. Technol. 2013, 148, 277-282.

Klinke, H. B. et al., Potential inhibitors from wet oxidation of wheat straw and their effect on ethanol production of *Saccharomyces cerevisiae*: Wet oxidation and fermentation by yeast. Biotechnol. Bioeng. 2003, 81, (6), 738-747.

Kontur, W. S. et al., Revised sequence and annotation of the Rhodobacter sphaeroides 2.4.1 genome. Journal of Bacteriology 2012, 194, 7016-7017.

Kumar, P. et al., Methods for Pretreatment of Lignocellulosic Biomass for Efficient Hydrolysis and Biofuel Production. Industrial & Engineering Chemistry Research 2009, 48, (8), 3713-3729.

Kuever, J. et al., Isolation and characterization of a new spore-forming sulfate-reducing bacterium growing by complete oxidation of catechol. Arch Microbiol. 1993;159(3):282-8.

Larimer, F. W. et al., Complete genome sequence of the metabolically versatile photosynthetic bacterium Rhodopseudomonas palustris. Nat. Biotechnol. 2004, 22, (1), 55-61.

Larsson, S. et al., Comparison of different methods for the detoxification of lignocellulose hydrolyzates of spruce. Appl. Biochem. Biotechnol. 1999, 77-9, 91-103.

Larsson, S. et al., Influence of lignocellulose-derived aromatic compounds on oxygen-limited growth and ethanolic fermentation by *Saccharomyces cerevisiae*. Appl Biochem Biotechnol 2000, 84-86, 617-32.

Lau, M. W. et al., Cellulosic ethanol production from AFEX-treated corn stover using *Saccharomyces cerevisiae* 424A(LNH-ST). Proc. Natl. Acad. Sci. USA 2009, 106, (5), 1368-1373.

Lemke, R. A. S. et al., Synthesis scanvenging role of furan fatty acids. Proc. Natl. Acad. Sci. USA 2014, 111, (33), E3450-E3457.

Lemmer, K. et al., Oxygen-dependent regulation of bacterial lipid production. J. Bacteriol. 2015, Online first, (3).

Lonergan, D. J. et al., Phylogenetic analysis of dissimilatory Fe(III)-reducing bacteria. J Bacteriol. Apr. 1996;178(8):2402-8.

Lovley, D. R. et al., *Geobacter metallireducens* gen. nov. sp. nov., a microorganism capable of coupling the complete oxidation of organic compounds to the reduction of iron and other metals. Arch Microbiol. 1993;159(4):336-44.

Lovley, D. R. et al., Anaerobic Oxidation of Toluene, Phenol, and p-Cresol by the Dissimilatory Iron-Reducing Organism, GS-15. Appl Environ Microbiol. Jun. 1990;56(6):1858-64.

Macala, G. S. et al., Hydrogen transfer from supercritical methanol over a solid base catalyst: A model for lignin depolymerization. *ChemSusChem*, 2009, 2, 215-217.

MacKenzie, C. et al., The home stretch, a first analysis of the nearly completed genome of Rhodobacter sphaeroides 2.4.1. Photosynthesis Res. 2001, 70, (1), 19-41.

Mountfort, D. O. et al., *Syntrophus buswelli* gen. nov., sp. nov.: a benzoate catabolizer from methanogenic ecosystems. Int. J. Syst. Bacteria 1984 34:216-217.

Nozawa T. et al., Anaerobic metabolim of phthalate and other aromatic compounds by a denitrifying bacterium. J Bacteriol. Dec. 1988;170(12):5778-84.

Okayama, H. et al., Nonradioactive detection of mutations in the human genome by allele-specific amplification. Journal of Laboratory and Clinical Medicine 1989, 114, (2), 105-113.

Palmqvist, E. et al., Fermentation of lignocellulosic hydrolysates. I: inhibition and detoxification. Bioresour. Technol. 2000, 74, (1), 17-24.

Pan, C. et al., Characterization of anaerobic catabolism of p-coumarate in Rhodopseudomonas palustris by integrating transcriptomics and quantitative proteomics. Mol. Cell. Proteomics 2008, 7, (5), 938-948.

Pan, X. J. et al., Role of functionalgroups in lignin inhibition of enzymatic hydrolysis of cellulose to glucose. J Biobased Mater Bioenergy, 2008, 2, 25-32.

Parawira, W. et al., Biotechnological strategies to overcome inhibitors in lignocellulose hydrolysates for ethanol production: review. Crit. Rev. Biotechnol. 2011, 31, (1), 20-31.

Pattathil, S., et al., Insights into plant cell wall structure, architecture, and integrity using glycome profiling of native and AFEX™-pretreated biomass. J. Exp. Bot., 2015, 66(14):4279-4294.

Phattarasukol, S. et al., Identification of a p-Coumarate Degradation Regulon in Rhodopseudomonas palustris by Xpression, an Integrated Tool for Prokaryotic RNA-Seq Data Processing. Appl. Environ. Microbiol. 2012, 78, (19), 6812-6818.

Piotrowski, J. S. et al., Death by a thousand cuts: the challenges and diverse landscape of lignocellulosic hydrolysate inhibitors. Frontiers in Microbiology 2014, 5.

(56) References Cited

PUBLICATIONS

Rabus, R. et al., Complete oxidation of toluene under stricktly anoxic conditions by a new sulfate-reducing bacterium. Appl. Environ Microbiol. May 1993;59(5):1444-51.

Ragauskas, A. J. et al., The path forward for biofuels and biomaterials. Science 2006, 311, (5760), 484-489.

Ragauskas, A., et al., Lignin valorization: Improving lignin processing in the biorefinery. J. et al., Sci., 2014, 344.

Rhee, S. K. et al., Anaerobic and aerobic degradation of pyridine by a newly isolated denitrifying bacterium. Appl Environ Microbiol. Jul. 1997;63(7):2578-85.

Sathitsuksanoh, N. et al., Lignin fate and characterization during ionic liquid biomass pretreatment for renewable chemicals and fuels production. Green Chem., 2014, 16, 1236-1247.

Sato, T. et al., Harnessing Genetic Diversity in *Saccharomyces cerevisiae* for Improved Fermentation of Xylose in Hydrolysates of Alkaline Hydrogen Peroxide Pretreated Biomass Appl Environ Microbiol 2014, 80, (2), 540-554.

Schennen, U. et al., Anaerobic degradation of 2-fluorobenzoate by benzoate-degrading, denitrifying bacteria. J Bacteriol. Jan. 1985;161(1):321-5.

Schnell, S. et al., Anaerobic degradation of aniline and dihydroxybenzenes by newly isolated sulfate-reducing bacteria and description of Desulfobacterium anilini. Arch Microbiol. 1989;152(6):556-63.

Schoëcke, L. (1997) Energetik des mathanogene Benzoatabbaus durch Syntrophus gentianae. Thesis, University of Konstanz.

Schoëcke, L. et al., Energetics of methanogenic benzoate degradation by Syntrophus gentianae in syntrophic coculture. Microbiology 1997 143:2345-2351.

Schuerch C., Plasticizing wood with liquid ammonia. J. Ind. Eng. Chem., 1963, 55:39.

Schwalbach, M. S. et al., Complex Physiology and Compound Stress Responses during Fermentation of Alkali-Pretreated Corn Stover Hydrolysate by an *Escherichia coli* Ethanologen. Appl. Environ. Microbiol. 2012, 78, (9), 3442-3457.

Sistrom, W. R., The kinetics of the synthesis of photopigments in Rhodopseudomonas spheroides. J Gen Microbiol 1962, 28, 607-16.

Song, B. et al., Identification of denitrifier strain T1 as *Thauera aromatics* and proposal for emendation of the genus *Thauera* definition. Int J Syst Bacteriol. Jul. 1998;48 Pt 3:889-94.

Springer, N. et al., *Azoarcus anaerobius* sp. nov., a resorcinol-degrading, strictly anaerobic, denitrifying bacterium. Int J Syst Bacteriol. Jul. 1998;48 Pt 3:953-6.

Swinnen, S. et al., The fraction of cells the resume growth after acetic acid addition is a strain-dependent parameter of acetic acid tolerance in *Saccharomyces cerevisiae*. FEMS Yeast Res. 2014, 14, (4), 642-653.

Szewzyk, U. et al., Complete oxidation of catechol by the strictly anarobic sulfate-reducing *Desulfobacterium catecholicum* sp. nov. Arch. Microbiol. 1987 147:163-168.

Teymouri, F. et al., Optimization of the ammonia fiber explosion (AFEX) treatment parameters for enzymatic hydrolysis of corn stover. Bioresour. Technol. 2005, 96, (18), 2014-2018.

The 110th Congress of the United States, Energy Independence and Security Act of 2007. Public Law 110-140. In 2007.

Trajano, H. et al., The fate of lignin during hydrothermal pretreatment. Biotechnol. Biofuels, 2013, 6, 110.

U.S. DOE Lignocellulosic biomass for advanced biofuels and bioproducts: Workshop Report, DOE/SC-0000; U. S. Department of Energy Office of Science: Washington D.C., 2014, http://genomicscience.energy.gov/biofuels/lignocellulose/.

USETA, International Energy Outlook 2011, 2011.

van Schie, P. M. et al., Isolation and characterization of phenol-degrading denitrifying bacteria. Appl Environ Microbiol. Jul. 1998;64(7):2432-8.

Verduyn, C. et al., Effect of benzoic acid of metabolic fluxes in yeasts: a continuous-culture study on the regulation of respiration and alcoholic fermentation. Yeast. Jul. 1992;8(7):501-17.

Warikoo, V, et al., Interspecies acetate transfer influences the extent of anaerobic benzoate degradation by syntrophic consortia. Appl Environ Microbiol. Jan. 1996;62(1):26-32.

Widdel, F. et al., Gram-negative mesophilic sulfate-reducing bacteria. (1992) In: The Prokaryotes (Balows, A., Trueper, H.G., Dworkin, M., Harder, W. and Schleifer, K.-H., Eds.), pp. 3352-3378. Springer, New York, NY.

Zakzeski, J. et al., The catalytic valorization of lignin for the production of renewable chemicals. Chem. Rev., 2010, 110, 3552-3599.

Zaldivar, J. et al., Effect of selected aldehydes on the gowth and fermentation of ethanologenic *Escherichia coli*. Biotechnol Bioeng 1999, 65, (1), 24-33.

Zhou, J., et al., Phylogenetic analyses of a new group of denitrifiers capable of anaerobic gowth of toluene and description of *Azoarcus tolulyticus* sp. nov. Int J Syst Bacteriol. Jul. 1995;45(3):500-6.

| Organic Carbon Sources | | | | | | | | |
|---|---|---|---|---|---|---|---|---|
| ⬡ | Benzoic Acid | Benz-aldehyde | Benzyl alcohol | Benz-amide | Cinnamic Acid | Cinnam-aldehyde | Cinnamic alcohol | Cinnamic amide |
| ⬡ | p-OH Benzoic Acid | p-OH Benz-aldehyde | p-OH Benzyl alcohol | p-OH Benz-amide | p-Coumaric Acid | Coum-aroyl aldehyde | Coum-aroyl alcohol | Coum-aroyl amide |
| ⬡ | Vanillic Acid | Vanillin | Vanillyl alcohol | Vanillyl amide | Ferulic Acid | Feruloyl aldehyde | Feruloyl alcohol | Feruloyl amide |
| ⬡ | Syringic Acid | Syring-aldehyde | Syringyl alcohol | Syringyl amide | Synapic Acid | Synapic aldehyde | Synapic alcohol | Synapic amide |

Figure 1

METHODS OF PROCESSING AROMATIC COMPOUNDS

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The present invention is directed to microbial methods of removing aromatic compounds from aromatic compound-containing solutions, such as lignocellulosic biomass hydrolysates and lignin extracts; transforming and concentrating the aromatic compounds; and/or converting the aromatic compounds into non-aromatic commodity chemicals.

BACKGROUND

The increasing world-wide demand for energy is accelerating fossil fuel consumption, depleting natural resources, and contributing to climate change (USEIA, 2011). With roughly 80% of the world's primary energy supply derived from fossil fuels, there is significant interest in increasing the contribution of renewable fuels to the overall energy production portfolio. Liquid fuels generated from lignocellulosic biomass are of particular interest as transportation fuels for long-term environmental and economic sustainability.

The Energy Independence and Security Act created a roadmap for increased industrial production of biofuels from cellulosic biomass in the United States (Public Law 110-140, 2007). According to the roadmap, the production of renewable fuels from cellulosic biomass was expected to reach 1.75 billion gallons by 2014 (Public Law 110-140, 2007). The actual production was only 683,643 gallons, (U.S. Environmental Protection Agency RFS2 Data, 2014) and the first generation of commercial-scale biorefineries in the U.S., to be in full operation in 2015, will not exceed an annual capacity of 50 million gallons (U.S. DOE, 2014).

Major bottlenecks still exist for the cost-effective production of biofuels from cellulosic biomass. Some of the challenges are economic and brought about by the massive amounts of fossil fuels that can now be tapped with horizontal drilling and hydraulic fracturing, which contribute to instability in the price of fossil fuels. Other challenges are technical, requiring new scientific and engineering innovation to bring transformational changes and cost reductions to the cellulosic biofuels industry.

One of the persistent challenges to implement cost-effective fermentation processes is the presence, in the hydrolysates derived from biomass, of plant-derived aromatic compounds and other small bioactive molecules produced during biomass deconstruction (Palmqvist et al. 2000, Piotrowski et al. 2014). Some of these molecules have been shown to diminish biofuel production by inhibiting growth and metabolism of sugars in fermenting organisms. For instance, acetic acid is known to affect cellular processes, reduce ethanol yields, and lower sugar consumption in wild type and engineered strains of *Saccharomyces cerevisiae*, (Bellissimi et al. 2009, Swinnen et al. 2014) whereas the negative effects of a variety of aromatic compounds on ethanologens such as *S. cerevisiae*, *Zymomonas mobilis*, and *Escherichia coli* are well documented (Chambel et al. 1999, Iwaki et al. 2013, Klinke et al. 2003, Delgenes et al. 1996, Zaldivar et al. 1999, Sato et al. 2014).

The suite of inhibitory molecules in hydrolysates is diverse (Piotrowski et al. 2014). Several strategies have been employed to overcome the effect of these inhibitory bioactive molecules (Larsson et al. 1999, Jonsson et al. 1998, Parawira et al. 2011). Although detoxification can be achieved by different approaches, in most cases the removal of the inhibitory compounds is accompanied by consumption of a significant amount of sugars (e.g., 5 to 35%) (Parawira et al. 2011).

There is a need to selectively remove inhibitory aromatic compounds from lignocellulosic biomass hydrolysates, lignin extracts, or other aromatic compound-containing solutions, without consuming the sugars needed for biofuel production. There is also a need of strategies to degrade or biotransform the large variety of plant-derived aromatics in lignocellulosic biomass hydrolysates, lignin extracts, or other aromatic compound-containing solutions into compounds that can be recovered and used for other applications.

SUMMARY OF THE INVENTION

The present invention provides methods of processing solutions comprising one or more aromatic compounds. One method comprises culturing a first microorganism capable of metabolizing at least one of the aromatic compounds in the solution for a time sufficient to reduce an amount of the aromatic compound and thereby generate a processed solution. The first microorganism in some versions comprises only a partial benzoyl-CoA pathway, which thereby results in the production of certain aromatic compounds. Some versions comprise culturing a second microorganism in the processed solution. The second microorganism may be sensitive to the aromatic compound reduced by the first microorganism.

In an exemplary embodiment, *Rhodopseudomonas palustris*, a bacterium that anaerobically degrades aromatic compounds and utilizes short chain organic acids, is used to selectively remove inhibitory molecules from biomass hydrolysate, without substantially consuming the sugars needed for biofuel production with other microorganisms. Another exemplary embodiment includes modification of selected enzymes in the benzoyl-CoA pathway of *R. palustris* to result in the biotransformation of the large variety of plant-derived aromatics into a single phenolic compound that can be recovered and used for other applications.

The methods provided herein add value to cellulosic biomass biorefineries, where production of multiple products is essential for the cost-effective and sustainable production of biofuels from cellulosic biomass.

The objects and advantages of the invention will appear more fully from the following detailed description of the preferred embodiment of the invention made in conjunction with the accompanying drawings.

BRIEF DESCRIPTION OF THE DRAWINGS

FIG. 1 shows exemplary aromatic compounds that can be included in solutions processed according to the methods of the present invention.

DETAILED DESCRIPTION OF THE INVENTION

Figure 2:
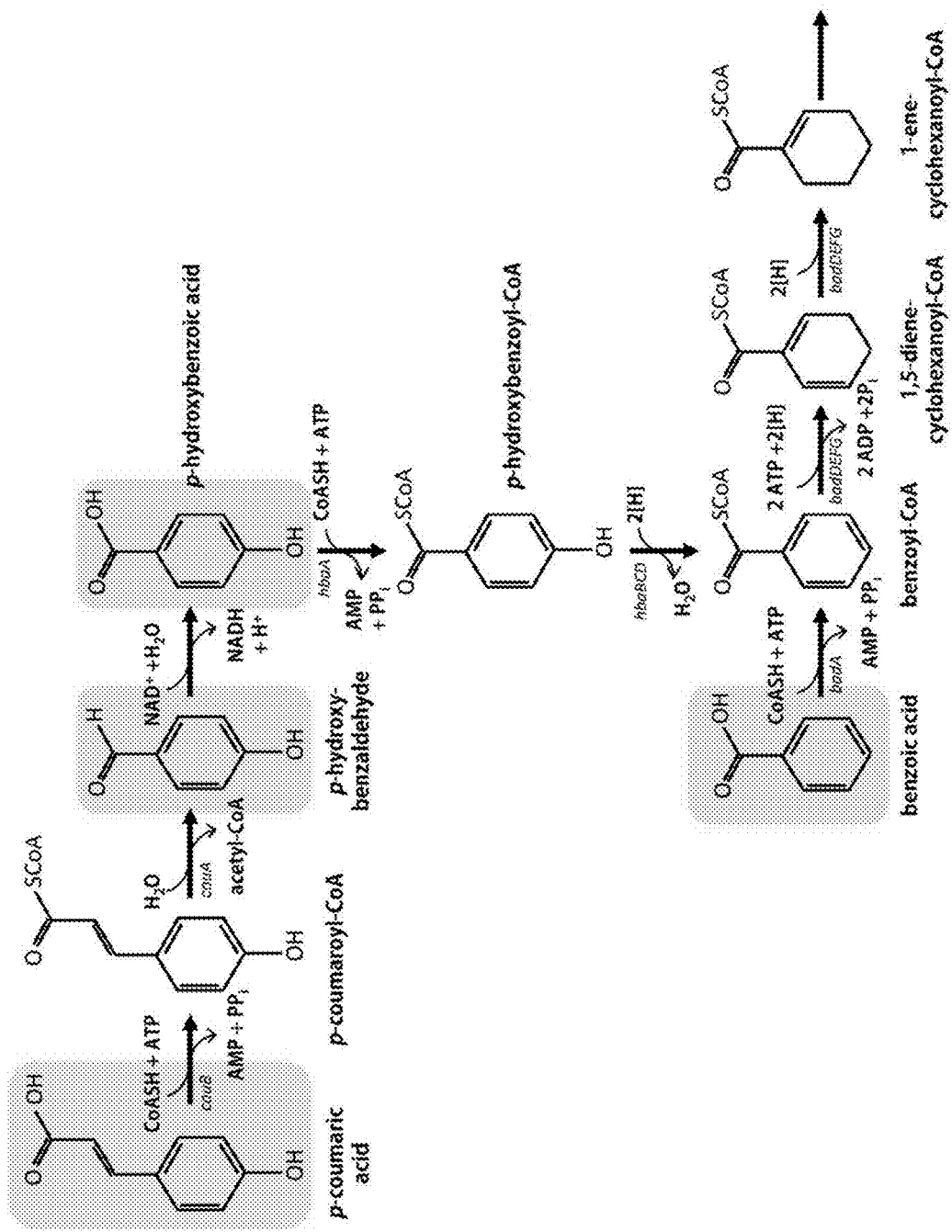
FIG. 2 shows pathways of aromatics degraded through the benzoyl-CoA pathway.

The invention provides methods of processing a solution comprising one or more aromatic compounds.

The aromatic compounds preferably comprise an aromatic ring with at least one of an aldehyde moiety, an amide moiety, a carboxylate moiety (encompassing acid and salt forms), or an alcohol (hydroxy) moiety either directly or indirectly bound to the aromatic ring. If indirectly bound, each aldehyde moiety, amide moiety, carboxylate moiety, or alcohol moiety is bound to the aromatic ring via an alkylene, alkenylene, or alkynylene group. The alkylene, alkenylene, or alkynylene groups may independently comprise from 1 to 12 carbons, more preferably from 1 to 6 carbons, and may be linear or branched.

The aromatic ring may be a monocyclic or polycyclic aromatic ring. Exemplary compounds include a six-membered, monocyclic aromatic ring. In addition to the aldehyde, amide, carboxylate or alcohol (hydroxy) moieties described above, the aromatic ring may be substituted in one or more positions with a substituent selected from the group consisting of alkyl, alkenyl, alkynyl, hydroxy, alkoxy, alkanoyl, alkanoyloxy, hydroxy-substituted alkoxy, hydroxy-substituted alkanoyl, hydroxy-substituted alkanoyloxy, aryl, and aryloxy groups. The alkyl, alkenyl, alkynyl, hydroxy, alkoxy, alkanoyl, alkanoyloxy, hydroxy-substituted alkoxy, hydroxy-substituted alkanoyl, hydroxy-substituted alkanoyloxy, aryl, and aryloxy groups may comprise from 1 to 12 carbons, more preferably from 1 to 6 carbons, and may be linear, branched, or cyclic. In preferred versions, the aromatic ring comprises at least one or at least two alkoxy groups directly bound thereto. The alkoxy groups are preferably methoxy groups.

In some versions, the six-membered ring may be in the form of a substituted or unsubstituted phenyl group, a substituted or unsubstituted 4-hydroxyphenyl group, a substituted or unsubstituted 4-hydroxy-3-alkoxyphenyl group, and a substituted or unsubstituted 4-hydroxy-3,5-dialkoxyphenyl group. The alkoxy moieties may have from 1 to 6 carbons. Methoxy groups are preferred. The substituents may be in one or more of the 2-6 positions on the ring, depending on the availability in the particular six-membered ring, and may be independently selected from the substituents described above.

Accordingly, the aromatic compound may be a selected from the group consisting of a substituted or unsubstituted phenyl amide, a substituted or unsubstituted phenyl aldehyde, a substituted or unsubstituted phenyl alcohol, a substituted or unsubstituted phenyl carboxylic acid, a substituted or unsubstituted 4-hydroxyphenyl amide, a substituted or unsubstituted 4-hydroxyphenyl aldehyde, a substituted or unsubstituted 4-hydroxyphenyl alcohol, a substituted or unsubstituted 4-hydroxyphenyl carboxylic acid, a substituted or unsubstituted 4-hydroxy-3-methoxyphenyl amide, a substituted or unsubstituted 4-hydroxy-3-methoxyphenyl aldehyde, a substituted or unsubstituted 4-hydroxy-3-methoxyphenyl alcohol, a substituted or unsubstituted 4-hydroxy-3-methoxyphenyl carboxylic acid, a substituted or unsubstituted 4-hydroxy-3,5-dimethoxyphenyl amide, a substituted or unsubstituted 4-hydroxy-3,5-dimethoxyphenyl aldehyde, a substituted or unsubstituted 4-hydroxy-3,5-dimethoxyphenyl alcohol, a substituted or unsubstituted 4-hydroxy-3,5-dimethoxyphenyl carboxylic acid, and combinations thereof.

In some versions of the invention, at least one aromatic compound has the formula:

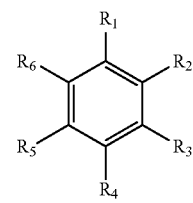

wherein $R_1$ is: carboxyl; aldehyde; amido; alkyl, alkenyl, or alkynyl alcohol; alkyl, alkenyl, or alkynyl carboxylic acid; alkyl, alkenyl, or alkynyl aldehyde; alkyl, alkenyl, alkynyl amide; or salts thereof; and $R_2$-$R_6$ are independently selected from the group consisting of hydrogen, alkyl, alkenyl, alkynyl, hydroxy, alkoxy, alkanoyl, alkanoyloxy, hydroxy-substituted alkoxy, hydroxy-substituted alkanoyl, hydroxy-substituted alkanoyloxy, aryl, and aryloxy.

In some versions, $R_1$ is selected from the group consisting of:

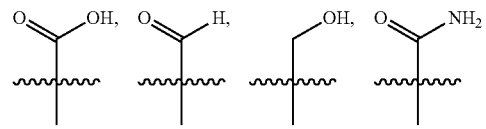

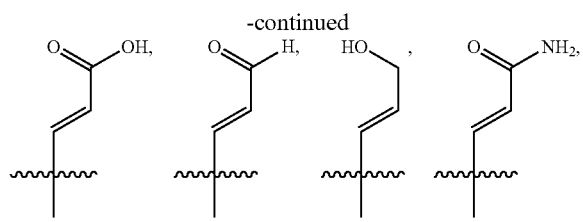

and salts thereof.

Exemplary aromatic compounds that can be included in the solution are shown in FIG. 1. These include benzoic acid, benzaldehyde, benzyl alcohol, benzamide, cinnamic acid, cinnamaldehyde, cinnamic alcohol, cinnamic amide, 4-hydroxybenzoic acid, 4-hydroxybenzaldehyde, 4-hydroxybenzyl alcohol, 4-hydroxybenzamide, p-coumaric acid, p-coumaroyl aldehyde, p-coumaroyl alcohol, p-coumaroyl amide, vanillic acid, vanillin, vanillyl alcohol, vanillyl amide, ferulic acid, feruloyl aldehyde, feruloyl alcohol, feruloyl amide, syringic acid, syringaldehyde, syringyl alcohol, syringyl amide, synapic acid, synapic aldehyde, synapic alcohol, synapic amide, and combinations thereof.

In some versions, the aromatic compound in the solution comprises at least one of p-coumaroyl amide, feruloyl amide, 4-hydroxybenzoic acid, p-coumaric acid, ferulic acid, 4-hydroxybenzaldehyde, vanillin, and syringaldehyde. In some versions, the aromatic compound in the solution comprises at least one of p-coumaroyl amide, feruloyl amide, vanillin, and syringaldehyde.

The solution may comprise at least 1, at least 2, at least 3, at least 4, at least 5, at least 6, at least 7, at least 8, at least 9, at least 10, at least 11, at least 12, at least 13, at least 14, at least 15, or at least 20 structurally different aromatic compounds having a structure as described herein.

The aromatic compound in the solution may be derived, purified, or semi-purified from biomass, such as lignocellulosic biomass. Biomass is biological material derived from living or once-living organisms. Biomass can be from plant, animal, or other organic material. Biomass is carbon based and is composed of a mixture of organic molecules containing hydrogen, usually including atoms of oxygen, often nitrogen and also small quantities of other atoms, including alkali, alkaline earth and heavy metals. Lignocellulosic biomass is biomass containing the carbohydrate polymers cellulose and hemicellulose and the aromatic polymer lignin. Non-limiting examples of biomass or lignocellulosic biomass include costal Bermuda grass, corn cobs, corn grain, corn stover, cotton seed hairs, grasses, hardwood (poplar, etc.), hardwood stems, leaves, newspaper, nut shells, paper, primary wastewater solids, softwood, softwood stems, solid cattle manure, sorted refuse, sugarcane, swine waste, switchgrass, waste papers from chemical pulps, wheat straw, wood, and woody residues.

In addition to the one or more aromatic compounds, the solution may comprise a fermentable sugar. The fermentable sugar is preferably present in an amount sufficient to support the growth of at least one microorganism. The fermentable sugar may be present in an amount of about 0.01% to about 99% by mass of total carbon content, about 0.05% to about 75% by mass of total carbon content, about 0.05% to about 50% by mass of total carbon content, about 0.05% to about 25% by mass of total carbon content, about 0.05% to about 10% by mass of total carbon content, about 0.05% to about 5% by mass of total carbon content, about 0.1% to about 2.5% by mass of total carbon content, or any combination thereof. The fermentable sugar may be present in an amount of about 0.01% to about 99% w/v, about 0.05% to about 75% w/v, about 0.05% to about 50% w/v, about 0.05% to about 25% w/v, about 0.05% to about 10% w/v, about 0.05% to about 5% w/v, about 0.1% to about 2.5% w/v, or any combination thereof. Non-limiting examples of fermentable sugars include adonitol, arabinose, arabitol, ascorbic acid, chitin, cellubiose, dulcitol, erythrulose, fructose, fucose, galactose, glucose, gluconate, inositol, lactose, lactulose, lyxose, maltitol, maltose, maltotriose, mannitol, mannose, melezitose, melibiose, palatinose, pentaerythritol, raffinose, rhamnose, ribose, sorbitol, sorbose, starch, sucrose, trehalose, xylitol, xylose, and hydrates thereof.

The solution may also or alternatively comprise acetate. The acetate may be present in an amount to support growth of at least one microorganism.

In some versions of the invention, the solution comprises processed biomass, such as processed lignocellulosic biomass, wherein the processed biomass itself comprises the one or more aromatic compounds. Processed lignocellulosic biomass includes lignocellulosic biomass that has been chemically, physically, or enzymatically treated. Examples of processed lignocellulosic biomass that may be included in the solution comprise pretreated lignocellulosic biomass, lignocellulosic biomass lignin extract, and lignocellulosic biomass hydrolysate. "Pretreated lignocellulosic biomass" includes the cellulose- and hemicellulose-rich portion of lignocellulosic biomass resulting from any biomass pretreatment, some of which are described below. "Lignocellulosic biomass lignin extract" refers to any enriched form of lignin derived from biomass using any available method. Exemplary lignin extracts include the lignin-enriched extract resulting from biomass pretreatment. "Lignocellulosic biomass hydrolysate" refers to biomass in which at least a portion of the cellulose and/or hemicellulose present in biomass has been hydrolyzed to simple sugars.

Pretreated lignocellulosic biomass and lignin extract suitable for use in the present invention may be obtained through any available method of biomass pretreatment. Pretreatment of biomass removes a large proportion of the lignin and other materials from the cellulose and hemicellulose and enhances the porosity of the biomass for optional downstream hydrolysis. The portion of biomass from which the lignin has been removed in the pretreatment process constitutes a suitable pretreated lignocellulosic biomass for use in the present invention. The removed lignin portion may constitutes an exemplary lignin extract suitable for use in the present invention. A variety of biomass pretreatments are well known in the art. Exemplary pretreatments include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, extractive ammonia (EA) pretreatment, and pulsed electrical field treatment, among others. See, e.g., Kumar et al. 2009 and da Costa Sousa et al. 2016. Methods of generating a lignin extract other than biomass pretreatment are also suitable.

Lignocellulosic biomass hydrolysate suitable for use in the invention may be obtained by hydrolyzing either pretreated or non-pretreated lignocellulosic biomass. Hydrolysis converts biomass polymers to fermentable sugars, such as glucose and xylose, and other monomeric or oligomeric components. Methods for hydrolyzing biomass, also known as saccharification, are well known in the art. Exemplary hydrolysis methods include enzymatic hydrolysis (e.g., with cellulases or other enzymes) and acid hydrolysis (e.g., with sulfurous, sulfuric, hydrochloric, hydrofluoric, phosphoric, nitric, and/or formic acids), among other methods.

In some versions, the solution may comprise, consist, or consist essentially of diluted pretreated lignocellulosic biomass, lignocellulosic biomass lignin extract, or lignocellulosic biomass hydrolysate. The diluted pretreated lignocellulosic biomass, lignocellulosic biomass lignin extract, or lignocellulosic biomass hydrolysate may comprise pretreated lignocellulosic biomass, lignocellulosic biomass lignin extract, or lignocellulosic biomass hydrolysate diluted with a solvent such as water or minimum medium. The solvent may be devoid or substantially devoid of fermentable sugars. Thus, in some versions of the invention, the solution comprises diluted pretreated lignocellulosic biomass, lignocellulosic biomass lignin extract, or lignocellulosic biomass hydrolysate wherein greater than about 1%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, or greater than about 99% by mass of total fermentable sugar in the solution is provided by the pretreated lignocellulosic biomass, lignocellulosic biomass lignin extract, or lignocellulosic biomass hydrolysate.

The methods of the invention include culturing a first microorganism in the solution comprising one or more aromatic compounds. The solution is preferably in the form of a medium suitable for culturing the first microorganism. The first microorganism may comprise any microorganism capable of metabolizing the aromatic compounds. The microorganism may metabolize the aromatic compound as a substrate for growth and/or may convert the aromatic compound to another compound. In the latter case, the microorganism may convert the aromatic compound to a non-aromatic compound or to another aromatic compound. The microorganism may be capable of metabolizing the aromatic compounds in aerobic conditions, anaerobic conditions, or both aerobic and anaerobic conditions. Microorganisms that metabolize the aromatic compounds in anaerobic conditions are preferred. Microorganisms that preferentially or exclusively metabolize aromatic compounds over fermentable sugars under anaerobic conditions are preferred. Microorganisms that are capable of growth on one or more aromatic compounds as the sole source of cell carbon are also preferred.

Microorganisms suitable as a first microorganism include a variety of bacteria, archaea, and fungi. Examples include proteobacteria, phototrophic bacteria, denitrifying bacteria, sulfate-reducing bacteria, iron-reducing bacteria (also known as iron bacteria), and fermentative bacteria (typically in syntrophic co-culture with a methanogenic or sulfate-reducing bacteria). Examples of phototropic bacteria include members of the genus *Rhodopseudomonas*, including *R. palustris*, among others. Examples of denitrifying bacteria include members of the genus *Thauera*, including *T. aromatica, T. selenatis*, and strain mXyN1; members of the genus *Azoarcus*, including *A. evansii, A. tolulyticus, A. anaerobius, A. indigens*, and strains ToN1, PbN1, ebN1, FL05, pF6, PH002, CR23, and FL05; members of the genus *Burkholderia*, including *B. cepacia*; and members of the genus *Alcaligenes*, including *A. xylosoxidans* subsp. *denitrificans* PN-1, among others. Examples of sulfate-reducing bacteria include members of the genus *Desulfobacterium*, including *D. phenolicum, D. catecholicum*, and *Desulfobacterium* sp. strain Cat2; members of the genus *Desulfobacula*, including *D. toluolica*; and strains Groll, Tol2, and PRTOL1, among others. Examples of iron-reducing bacteria includes members of the genus *Geobacter*, including *G. metallireducens*; members of the genera *Desulfuromonas, Pelobacter*, and *Desulfuromusa*; and strain GS-15, among others. Examples of fermentative bacteria include members of the genus *Syntrophus*, including *S. buselli* and *S. gentianae*, and strains SB and PA-1, among others. Additional examples of suitable first microorganisms include members of the genus *Pseudomonas*, including *P. aeruginosa, P. stutzeri*, and strains KB650, KB740, KB820, and P136, among others.

In some versions of the invention, suitable first microorganisms are those that have a benzoyl-CoA pathway. The benzoyl-CoA pathway, sometimes referred to as the "central benzoyl-CoA pathway," is a well-characterized pathway that metabolizes benzoic acid and related aromatic compounds by converting them to CoA intermediates prior to downstream metabolism. See Harwood et al. 1988, Dutton et al. 1969, Breese et al. 1998, Harwood et al. 1998, and Gall et al. 2013. As used herein "benzoyl-CoA pathway" refers to a collection of enzymes that includes one or more of a 4-hydroxybenzoate-CoA ligase (EC 6.2.1.27), a benzoate-CoA ligase (EC 6.2.1.25), a 3-hydroxybenzoate-CoA ligase (EC 6.2.1.37), a 4-hydroxybenzoyl-CoA reductase (EC 1.3.7.9), and a benzoyl-CoA reductase (EC 1.3.7.8). Suitable first microorganisms of the invention express one or all of the above-referenced enzymes. In some versions of the invention, the first microorganism expresses at least one or more of a 4-hydroxybenzoate-CoA ligase (EC 6.2.1.27), a benzoate-CoA ligase (EC 6.2.1.25), and a 3-hydroxybenzoate-CoA ligase (EC 6.2.1.37).

One or more of the enzymes in the benzoyl-CoA pathway are naturally expressed by a number of microorganisms, including but not limited to members of the genus *Acidovorax*; members of the genus *Azoarcus*, including *A. evansii, A. toluclasticus, A. tolulyticus, A. toluvorans*, and *Azoarcus* sp. CIB; members of the genus *Burkholderia*, including *B. xenovorans*; members of the genus *Centaurium*, including *C. erythraea*; members of the genus *Clarkia*, including *C. breweri*; members of the genus *Desulfovibrio*; members of the genus *Geobacter*, including *G. metallireducens*; members of the genus *Hypericum*, including *H. androsaemum*; members of the genus *Magnetospirillum*, including *M. magnetotacticum* and *M. hungatei*; members of the genus *Nicotiana*, including *N. tabacum*; members of the genus *Pseudomonas*; members of the genus *Rhodopseudomonas*, including *R. palustris*; members of the genus *Streptomyces*, including *S. maritimus*; members of the genus *Syntrophus*, including *S. aciditrophicus*; members of the genus *Thauera*, including *T. aromaticak, T. chlorobenzoica*, and *T. selenatis*; and members of the genus *Xanthomonas*, including *X. albilineans*; among others. Each of these microorganisms constitutes a suitable first microorganism. Suitable first microorganisms also include microorganisms that do not naturally express any benzoyl-CoA pathway enzymes but are genetically engineered to do so. Suitable first microorganisms also include microorganisms that naturally express only a subset of the benzoyl-CoA pathway enzymes but are genetically engineered to express additional benzoyl-CoA pathway enzymes.

In *R. palustris*, the 4-hydroxybenzoate-CoA ligase (EC 6.2.1.27) is HbaA, which is encoded by hbaA; the benzoate-CoA ligase (EC 6.2.1.25) is BadA, which is encoded by badA; the 4-hydroxybenzoyl-CoA reductase (EC 1.3.7.9) is hbaBCD, which is encoded by hbaBCD; and the benzoyl-CoA reductase (EC 1.3.7.8) is BadDEFG, which is encoded by badDEFG. In *R. palustris*, as with other organisms, para-dehydroxylation of meta-,para-dihydroxybenzoyl-CoA is carried out by the 4-hydroxybenzoyl-CoA reductase (EC 1.3.7.9), and dearomatization of the resulting meta-hydroxybenzoyl-CoA is carried out by the benzoyl-CoA reductase (EC 1.3.7.8). The benzoyl-CoA pathway enzymes in other microorganisms, such as *Azoarcus, Thauera*, and the others mentioned herein, are well known in the art. The genes for any of these enzymes can be expressed in microorganisms not naturally expressing them using well-known molecular biology techniques to generate a suitable first microorganism.

In some versions of the invention, the first microorganism expresses only a subset of the enzymes in the benzoyl-CoA pathway, wherein at least one of the 4-hydroxybenzoate-CoA ligase (EC 6.2.1.27), the benzoate-CoA ligase (EC 6.2.1.25), the 3-hydroxybenzoate-CoA ligase (EC 6.2.1.37), the 4-hydroxybenzoyl-CoA reductase (EC 1.3.7.9), and the benzoyl-CoA reductase (EC 1.3.7.8) is entirely absent from the microorganism or is non-functional. Such a first microorganism can be generated by mutating one or more genes of benzoyl-CoA pathway enzymes in a microorganism that naturally expresses the enzymes, by ectopically expressing only a subset of benzoyl-CoA pathway enzymes in a microorganism that does not naturally express the benzoyl-CoA pathway enzymes, or by other methods. In some versions of the invention, one or more of a 4-hydroxybenzoyl-CoA reductase (EC 1.3.7.9) and a benzoyl-CoA reductase (EC 1.3.7.8) is entirely absent from the microorganism or is non-functional. For the purposes herein, a microorganism that expresses a mutated form of an enzyme that is non-functional is considered not to express the enzyme. In some versions of the invention, at least one naturally expressed enzyme in the benzoyl-CoA pathway is mutated merely to attenuate its activity.

An exemplary version of a first microorganism that expresses only a subset of the enzymes in the benzoyl-CoA pathway is the *R. palustris* mutant CGA606 as a first microorganism that lacks a functional benzoyl-CoA reductase (EC 1.3.7.8) due to an insertion in the badE gene. The same effect in *R. palustris* can be obtained by mutating any of the other genes in the BadDEFG benzoyl-CoA reductase, such as badD, badF, badG, or the entire badDEFG gene cluster. Analogous mutations can be performed in the benzoyl-CoA reductase genes of other microorganisms that naturally express them.

Another exemplary version of a first microorganism that expresses only a subset of the enzymes in the benzoyl-CoA pathway is the *R. palustris* mutant CGA506 as a first microorganism that lacks a functional 4-hydroxybenzoyl-CoA reductase (EC 1.3.7.9) due to mutation of the hbaB gene. The same effect in *R. palustris* can be obtained by mutating any of the genes in the hbaBCD 4-hydroxybenzoyl-CoA reductase, such as hbaC, hbaD, or the entire hbaBCD gene cluster. Analogous mutations can be performed in the 4-hydroxybenzoyl-CoA reductase genes of other microorganisms that naturally express them.

A first microorganism that expresses only a subset of the benzoyl-CoA pathway allows for production of compounds, such as phenolic compounds, that can be recovered for various applications. As shown in the following examples, the CGA606 *R. palustris* mutant lacking a functional benzoyl-CoA reductase (EC 1.3.7.8) produces benzoic acid. The CGA506 *R. palustris* mutant lacking a functional 4-hydroxybenzoyl-CoA reductase (EC 1.3.7.9) produces 4-hydroxybenzoic acid.

The first microorganism may be cultured in a solution containing aromatic compounds to reduce the amount of one or more of the aromatic compounds in the solution. A solution in which an aromatic compound has been reduced by culturing a first microorganism is referred to herein as a "processed solution."

The first microorganism may reduce the one or more aromatic compounds in the solution by any amount. In preferred versions of the invention, the first microorganism reduces the amount of the one or more aromatic compounds by at least about 1%, at least about 5%, at least about 10%, at least about 15%, at least about 20%, at least about 30%, at least about 40%, at least about 50%, at least about 60%, at least about 70%, at least about 80%, at least about 90% or more by mass. Accordingly, the processed solution has at least about 99%, at least about 95%, at least about 90%, at least about 80%, at least about 70%, at least about 60%, at least about 50%, at least about 40%, at least about 30%, at least about 20%, at least about 10%, or less by mass of the one or more aromatic compounds than the starting solution.

In some versions of the invention, the first microorganism removes at least about 1%, at least about 5%, at least about 10%, at least about 15%, at least about 20%, at least about 30%, at least about 40%, at least about 50%, at least about 60%, at least about 70%, at least about 80%, at least about 90%, or more by mass of total aromatic compounds from the solution.

In certain versions of the invention, the first microorganism preferentially consumes aromatic compounds over sugars, at least in some conditions such as anaerobic conditions. In such versions, culturing the first microorganism either does not reduce or only minimally reduces the amount of sugars during the culturing. The amount of fermentable sugar is preferably reduced by no more than about 0%, no more than about 1%, no more than about 5%, no more than about 10%, no more than about 15%, no more than about 20%, no more than about 30%, no more than about 40%, no more than about 50%, no more than about 60%, no more than about 70%, no more than about 80%, no more than about 90% by mass. Accordingly, the processed solution has about 99%, about 95%, about 90%, about 80%, about 70%, about 60%, about 50%, about 40%, or about 30%, about 20%, about 10%, or more by mass of the amount of fermentable sugar in the starting solution. It is preferred that, if the fermentable sugar is reduced by the first microorganism, it is proportionally reduced to a lesser extent than the reduced aromatic compound. For example, if the first microorganism reduces an aromatic compound by at least about 20% by mass over a given time period, the fermentable sugars are reduced by less than about 20% by mass.

Some versions of the invention further include culturing a second microorganism in the processed solution. The processed solution is preferably a medium suitable for culturing the second microorganism. The second microorganism may be sensitive to one or more of the aromatic compounds reduced by the first microorganism. The term "sensitive" used in this context means that the second organism exhibits inhibited or reduced growth or inhibited or reduced sugar consumption in the presence of an amount of the aromatic compound present in the initial solution. By reducing the aromatic compounds, the first microorganism provides for enhanced growth of the second microorganism in the processed solution with respect to the level of growth that would occur in the initial solution. The second microorganism is preferably added to the processed solution but may be added to the initial solution provided a minimal amount is capable of surviving until the initial solution is suitably processed for enhanced growth of the second microorganism. In some versions of the invention, the second microorganism added to the processed solution after the first microorganism has removed at least about 1%, at least about 5%, at least about 10%, at least about 15%, at least about 20%, at least about 30%, at least about 40%, at least about 50%, at least about 60%, at least about 70%, at least about 80%, at least about 90% or more by mass of the one or more aromatic compounds from the solution.

In versions of the invention in which the first microorganism preferentially metabolizes aromatic compounds over fermentable sugars, the second microorganism is preferably capable of growth using fermentable sugar as a substrate. In this manner, the first microorganism removes compounds inhibitory to the second microorganism while leaving growth substrate for the second microorganism largely unconsumed. Thus, the second microorganism may be cultured in the processed solution without adding an external source of sugar either to the processed solution or to the starting solution. If any fermentable sugar is added, it is preferred that the amount of added fermentable sugar is less than about 1000-fold, less than about 300-fold, less than about 100-fold, less than about 30-fold, less than about 10-fold, less than about 3-fold, less than about 1-fold, less than about 0.3-fold, less than about 0.1-fold, less than about 0.03-fold, less than about 0.01-fold, less than 0.003-fold, or less than 0.001-fold by mass than the total amount of fermentable sugar consumed by the first microorganism and the second microorganism. In versions of the invention in which the solution comprises diluted pretreated lignocellulosic biomass, lignocellulosic biomass lignin extract, or lignocellulosic biomass hydrolysate, greater than about 1%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, or greater than about 99% by mass of total fermentable sugar in the solution and the processed solution throughout the culturing of the first microorganism and the second microorganism is provided by the pretreated lignocellulosic biomass, lignocellulosic biomass lignin extract, or lignocellulosic biomass hydrolysate.

The second microorganism is preferably one capable of producing one or more commodity chemicals by growing on the substrate not consumed by the first microorganism. As used herein, "commodity chemical" includes any compound capable of being purified or semi-purified and used for a downstream application. The commodity chemicals may be used as fuel, as reagents for synthesizing other compounds or materials, or for any other use. A large number of microorganisms capable of producing commodity chemicals by growing on fermentable sugars are known. These include bacteria and yeast. *Saccharomyces cerevisiae, Zymomonas mobilis,* and *Escherichia coli,* for example, are well-known ethanologens that can be used to produce ethanol. *Rhodobacter sphaeroides* can be used to produce long-chain fatty acids and furans (Lemke et al. 2014 and Lemmer et al. 2015). *E. coli* and other microorganisms can be used to produce polyhydroxyalkanoates (US Publication 2014/0073022). *E. coli* and other microorganisms can be used to produce fatty acids (U.S. Pat. No. 8,617,856). Other examples are well known in the art. The commodity chemical may be an aromatic or a non-aromatic compound.

One or both of the first and second microorganisms may be modified versions of parent microorganisms. For example, the first microorganism may be a microorganism that is genetically modified to functionally delete one or more of a 4-hydroxybenzoate-CoA ligase (EC 6.2.1.27), a benzoate-CoA ligase (EC 6.2.1.25), a 3-hydroxybenzoate-CoA ligase (EC 6.2.1.37), a 4-hydroxybenzoyl-CoA reductase (EC 1.3.7.9), and a benzoyl-CoA reductase (EC 1.3.7.8). For microorganisms in which the above-mentioned enzymes are multi-subunit enzymes encoded by more than one gene, such as the hbaBCD 4-hydroxybenzoyl-CoA reductase (EC 1.3.7.9) of *R. palustris* encoded by the hbaBCD gene cluster and the BadDEFG benzoyl-CoA reductase (EC 1.3.7.8) of *R. palustris* encoded by the badDEFG gene cluster, functionally deleting the enzyme can be accomplished by mutating the genes for any one, more than one, or all of the subunits.

As used herein, "functional deletion" of a gene product refers to any modification that reduces or ablates the activity of the gene product. "Gene product" refers to a protein or polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations (e.g., substitutions, partial or complete deletions, insertions, or other variations) to a coding sequence or a sequence controlling the transcription or translation of a coding sequence; placing a coding sequence under the control of a less active promoter; blocking transcription of the gene with a trans-acting DNA binding protein such as a TAL effector or CRISPR guided Cas9; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual,* 4$^{th}$ ed., Cold Spring Harbor Laboratory Press (2012) and Sambrook et al., *Molecular Cloning: A Laboratory Manual,* 3$^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or otherwise mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or otherwise mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or otherwise mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or otherwise mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene or coding sequence in its unaltered state as found in nature. In certain versions, the genetic modifications giving rise to a functionally deleted gene product are determined with respect to the gene or coding sequence in its form in a corresponding microorganism.

As used herein, "corresponding microorganism" refers to a microorganism of the same species having the same or substantially same genetic and proteomic composition as a microorganism of the invention, with the exception of genetic and proteomic differences resulting from the modifications described herein for the microorganisms of the invention.

The invention encompasses functionally deleting homologs of the genes or gene products explicitly described herein. Homologs include genes or gene products that are derived, naturally or artificially, from a common ancestral gene or gene product. Homology is generally inferred from sequence similarity between two or more genes or gene products. Homology between genes may be inferred from sequence similarity between the products of the genes. The precise percentage of similarity between sequences that is useful in establishing homology varies with the gene or gene product at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the coding sequences, genes, or gene products described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the coding sequences, genes, or gene products, respectively, described herein. In some versions, homologs of the genes described herein include genes that have gene products at least about 30%, 35%, 40%, 45%, 50%, 55%, 60%, 65%, 70%, 75%, 80%, 85%, 90%, 95%, or 99% identical to the gene products of the genes described herein. Methods for determining sequence similarity percentages (e.g., BLASTP and BLASTN using default parameters) are described herein and are generally available. The homologous gene products should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs."

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to coding sequences, genes, or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, at least about 65%, at least about 70%, at least about 75%, at least about 80%, at least about 85%, at least about 90, at least about 95%, at least about 98%, or at least about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Accordingly, homologs of the genes described herein include genes with gene products at least about 80%, at least about 85%, at least about 90%, at least about 95%, at least about 97%, at least about 98%, at least about 99%, or more identical to the gene products of the genes described herein.

The microorganisms of the invention may be modified to increase expression of one or more of the genes described herein or homologs thereof. Modifying the microorganism to increase expression of a gene can be performed using any suitable methods. Examples include genetically modifying the microorganism and culturing the microorganism in the presence of factors that increase expression of the gene. Suitable methods for genetic modification include but are not limited to placing the coding sequence under the control of a more active promoter, increasing the copy number of the gene, and/or introducing a translational enhancer on the gene (see, e.g., Olins et al. *Journal of Biological Chemistry*, 1989, 264(29):16973-16976). Increasing the copy number of the gene can be performed by introducing additional copies of the gene to the microorganism, i.e., by incorporating one or more exogenous copies of the native gene or a heterologous homolog thereof into the microbial genome, by introducing such copies to the microorganism on a plasmid or other vector, or by other means. "Exogenous" used in reference to a genetic element means the genetic element is introduced to a microorganism by genetic modification. "Heterologous" used in reference to a genetic element means that the genetic element is derived from a different species. A promoter that controls a particular coding sequence is herein described as being "operationally connected" to the coding sequence.

The microorganisms of the invention may include at least one recombinant nucleic acid configured to express or overexpress a particular enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress an enzyme produces the enzyme at a greater amount than a microorganism that does not include the recombinant nucleic acid.

Exogenous, heterologous nucleic acids encoding enzymes to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

The first microorganism may be modified to harbor one or more of the hbaA gene of R. palustris for expressing the HbaA 4-hydroxybenzoate-CoA ligase (EC 6.2.1.27), the badA gene of R. palustris for expressing the BadA benzoate-CoA ligase (EC 6.2.1.25), the hbaBCD gene cluster of R. palustris for expressing the hbaBCD 4-hydroxybenzoyl-CoA reductase (EC 1.3.7.9), and the badDEFG gene cluster of R. palustris for expressing the BadDEFG benzoyl-CoA reductase (EC 1.3.7.8) or homologs thereof. The gene clusters encoding hbaBCD and BadDEFG may be provided as a gene cassette or as individual genes (e.g., hbaBCD or hbaB, hbaC, and hbaD; badDEFG or badD, badE, badF, and badG). Each of the above-mentioned genes has been cloned and sequenced. Corresponding genes from other organisms, including those from Azoarcus, Thauera, and other organisms, have also been cloned and sequenced and can be used in place of the above-mentioned genes from R. palustris.

The term "increase," whether used to refer to an increase in production of a compound, an increase in expression of an enzyme, etc., generally refers to an increase from a baseline amount, whether the baseline amount is a positive amount or none at all.

Percentages expressed herein refer to percent by mass unless the context indicates otherwise.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1

Summary

Lignocellulosic biomass hydrolysates hold great potential as a feedstock for microbial biofuel production, due to their high concentration of fermentable sugars. Present at much lower concentrations are lignin-derived aromatic compounds that inhibit the growth and activity of biofuel-producing microbes. The following examples provide a microbial-mediated strategy for selectively removing these aromatic toxins, using the purple non-sulfur bacterium *Rhodopseudomonas palustris*. When grown photoheterotrophically in an anaerobic environment, *R. palustris* selectively removes most of the aromatics from ammonia fiber expansion (AFEX) treated corn stover hydrolysate (ACSH), while leaving the sugars mostly intact. Pre-treatment of ACSH with *R. palustris* greatly increases the growth and sugar utilization of a second microbe. We show that *R. palustris* can accommodate a host of growth substrates that have been previously described as unable to support growth, such as methoxylated aromatics, and those that have not yet been tested, such as aromatic amides. Further exploration indicates that most of these compounds are shown to be eventually shuttled to the benzoyl-CoA pathway for ring cleavage. Deletion of key enzymes in this pathway prevents total degradation of the aromatics in hydrolysate, and instead produces an avenue for transformation of this suite of aromatics into a single compound.

Methods

Corn Stover Hydrolysate.

Ammonia fiber expansion (AFEX) (Lau et al. 2009)—pretreated corn stover hydrolysate (ACSH) was prepared as described by (Schwalbach et al. 2012) and diluted with sterile deionized water to reach ~2% w/v sugars. The hydrolysates were filtered in series through 0.5 μm and 0.22 μm filters (Nalgene Disposable Bottle Top Filter, Thermo Fisher Scientific, Waltham, Mass.) prior to storage at 4° C. Before inoculation, the pH of each hydrolysate batch, originally between 4.6 and 4.8, was adjusted to 7.0 using potassium hydroxide (KOH) pellets. After pH adjustment, the hydrolysates were filter-sterilized by passing through 0.22 μm filters.

Microbial Strains.

*R. palustris* CGA009 (Larimer et al. 2004) *R. palustris* CGA606 (CGA009-derived mutant lacking benzoyl-CoA reductase activity) (Egland et al. 1997), and *R. palustris* CGA506 (CGA009-derived mutant lacking 4-hydroxybenzoyl-CoA reductase activity) (Gibson et al. 1997) were used in this study.

In addition, *R. sphaeroides* 241EDD, an *R. sphaeroides* 2.4.1-derived mutant with a modification in the edd gene (Mackenzie et al. 2001, Kontur et al. 2012) was also used. *R. sphaeroides* strain 2.4.1 has a single base pair insertion in the gene edd (RSP_2646, encoding KDPG dehydratase, accession number CP000143.2) relative to most other *R. sphaeroides* strains for which a genomic sequence is publicly available (RSKD131_0957 in *R. sphaeroides* KD131, accession number CP001150.1; Rsph17029_1303 in *R. sphaeroides* ATCC17029, accession number CP000577.1; Rsph17025_1181 in *R. sphaeroides* ATCC17025, accession number CP000661.1; RSWS8N_03435 in *R. sphaeroides* WS8N, accession number CM001161.1) (Lim et al. 2009, Porter et al. 2011). Thus, the edd gene of 2.4.1 was replaced with the gene from strain 2.4.1Ga (Cohen-Bazire et al. 1957), which lacks this single base insertion. Primers were designed to PCR amplify a region of the 2.4.1Ga genome extending from 842 bp upstream of the edd gene to 984 bp downstream of the gene. The upstream primer included a recognition site for HindIII (CGAT aAgCTTCGAGCTCACATTGACG) (SEQ ID NO:1), and the downstream primer included a recognition site for XbaI (GTACATCtCtaGATCGGCTGCGCTGAAG) (SEQ ID NO:2). This amplified fragment was digested with HindIII and XbaI and ligated into HindIII- and XbaI-digested pK18mobsacB (Schafer 1994) to produce plasmid pK18-Gaedd. This plasmid was mobilized from *Escherichia coli* strain S 17-1 into *R. sphaeroides* strain 2.4.1 via conjugation. Colonies of 2.4.1 in which pK18-Gaedd had been integrated into the genome via homologous recombination were selected for based on resistance to 25 g mL$^{-1}$ kanamycin and sensitivity to 10% sucrose. This strain was grown aerobically in SIS for two days to allow for excision of the plasmid from the genome via a second occurrence of homologous recombination. Colonies in which the plasmid had been excised from the genome were selected for by growth on SIS plates containing 10% sucrose. Colonies that contained the Ga version of the edd gene in their genome were determined via Sanger sequencing, and one of these strains, referred to as *R. sphaeroides* 241EDD, was used in these examples.

Minimal Media.

Photosynthetic medium (PM) prepared as described in (Kim et al. 1991) and containing succinate as the organic substrate, was used for *R. palustris* growth before inoculation in hydrolysate. Sistrom's minimal medium (SIS) containing succinate as the organic substrate, prepared as previously described (Sistrom 1962), was used for growing cultures of *R. sphaeroides* before inoculation into hydrolysate.

Experimental Conditions.

Most experiments were conducted in an Applikon biofermenter (3L Autoclavable Microbial BioBundle, Applikon Biotechnology, Foster City, Calif. 94404) using 1,000 mL of ACSH. In these experiments the pH was controlled between 6.95 and 7.1 with 1M $H_2SO_4$ and 10M KOH, and the cultures were placed in front of continuous light generated by 10 W tungsten lamps. The temperature was kept at 28° C., oxygen was removed by flushing with $N_2$ gas, and cell densities were measured using the Klett-Summerson colorimeter with a no. 66 filter (Klett MFG Co., NY). *R. sphaeroides* 241EDD and *R. palustris* CGA009 were pregrown in minimal media, and for each inoculation, 20 mL of culture were added to 1,000 mL of ACSH.

Experiments with *R. palustris* CGA506 and CGA606 were conducted with two-fold diluted ACSH (~1% glucose content) in the presence of 100 μg kanamycin mL$^{-1}$. The strain was pre-grown in PM, and for each incubation, 150 μL of culture were added to 15 mL of hydrolysate. Reactor tubes were closed with rubber stoppers to ensure anaerobic conditions and placed in continuous illumination at 30° C.

Analytical Procedures.

Organic acids and sugars were analyzed by high performance liquid chromatography (HPLC) and quantified with a refractive index detector (RID-10A, Shimadzu) using a Bio-Rad Aminex HPX-87H column at 60° C. and mobile phase of 5 mM $H_2SO_4$ at 0.6 mL/min as described by Schwalbach et al. 2012. Samples were prepared by filtering aliquots of the culture and diluting the filtrate ten-fold before injection into the HPLC. The majority of phenolic compounds were quantified by reverse phase HPLC—high resolution/accurate mass spectrometry, as described in Keating et al. 2014. Benzoic acid and 4-hydroxybenzoic acid were measured by high performance anion exchange chromatography—tandem mass spectrometry, using procedures also described in Keating et al. 2014.

Results and Discussion

Degradation of Plant-Derived Aromatics in Corn Stover Hydrolysates by *R. palustris* CGA009.

An effective microbial strategy to remove aromatic inhibitors from hydrolysates preferably employs an organism that specifically degrades aromatic compounds without utilizing glucose and xylose, the sugars used for biofuel production. In addition to being deficient in sugar utilization (Larimer et al. 2004), *R. palustris* CGA009 efficiently grows using short chain organic acids (Barbosa et al. 2001) and utilizes aromatic compounds as sole carbon sources under anaerobic conditions, using the benzoyl-CoA pathway (Harwood et al. 1988, Dutton et al. 1969, Harwood et al. 1998). Entrance into this pathway (FIG. 2) occurs through activation of benzoate, p-hydroxybenzoate, or similar compounds by ligation to Coenzyme A (CoA). A subsequent stepwise reduction of the aromatic ring yields 1-ene-cyclohexanoyl-CoA, leading to ring cleavage and further transformations to metabolites that enter central metabolism (England et al. 1997, Harrison et al. 2005, Humpula et al., 2011).

Figure 3:
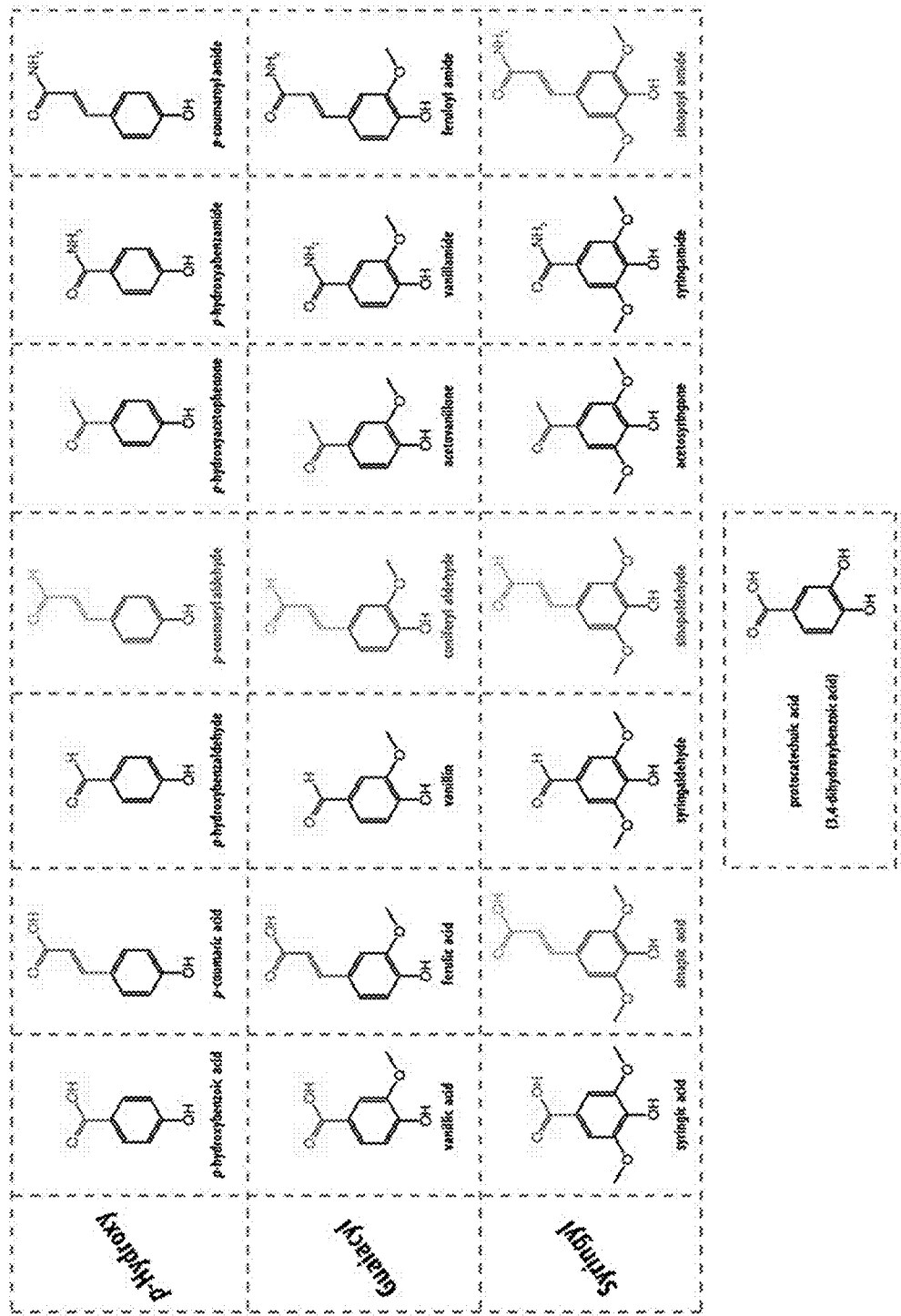
FIG. 3 shows names and chemical structures of aromatic compounds found in lignocellulosic hydrolysates.
Figure 4:
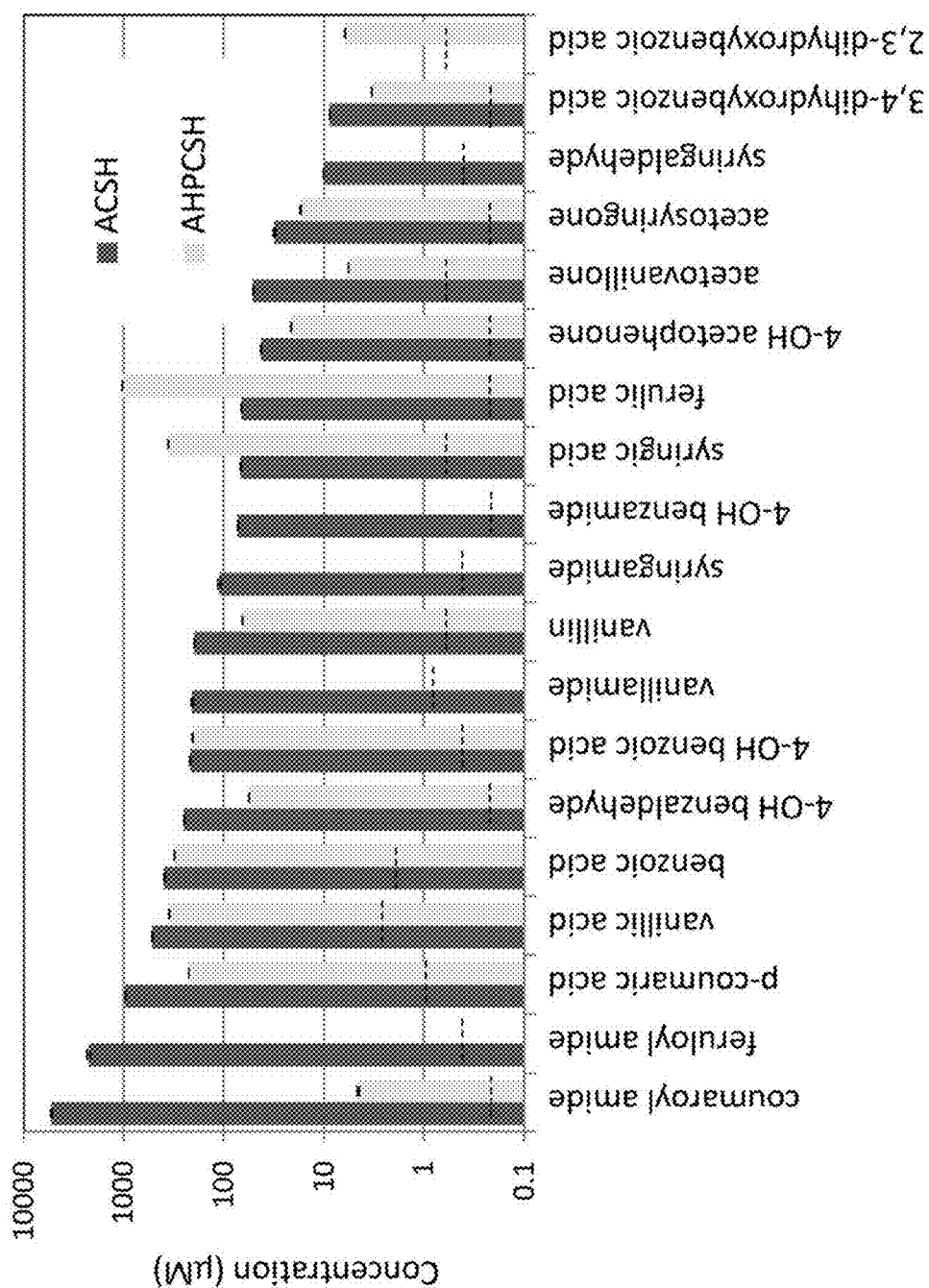
FIG. 4 shows concentrations of aromatic compounds in ammonia fiber expansion pretreated corn stover hydrolysate (ACSH) and alkaline hydrogen peroxide pretreated corn stover hydrolysate (AHPCSH). The dotted line for each compound denotes the detection limit. Other aromatics tested that were analyzed but found to be below detection limit include 3-hydroxybenzoic acid, vanillyl alcohol, syringyl alcohol, 4-hydroxybenzyl alcohol, and sinapic acid.

Although *R. palustris* CGA009 has been shown to degrade several aromatic hydrocarbons (Table 1), little is known about its ability to utilize more complex plant-derived aromatics present in hydrolysates (FIGS. 3 and 4), which contain up to two methoxy functional groups and an alkyl side-chain with characteristics that depend on the methods used for biomass deconstruction (Piotrowski et al. 2014). In general, *R. palustris* CGA009 has been shown to completely degrade phenolic acids without ring substitutions or with only one hydroxyl group in the meta or para position (Table 1) (Harwood et al. 1988). In addition, of the phenolic acids with a propanoid side-chain, p-coumaric acid can be completely degraded by R. palustris GGA009 (FIG. 2) (Hirakawa et al. 2012), while only partial degradation, without ring fission, was shown to occur with acids having more than one ring substitution, such as ferulic or caffeic acid (Table 1). R. palustris CGA009 has also been reported not to grow on vanillin, vanillic acid, or syringic acid (Harwood et al. 1988). Growth of R. palustris CGA009 on the aromatic amides that are not only found in hydrolysates prepared with the AFEX pretreatment (Lau et al. 2009) but also known to have inhibitory effects on ethanologenic organisms (Piotrowski et al. 2014) has not been investigated.

TABLE 1

Anaerobic transformation of aromatic compounds by R. palustris CGA009*

| Compound | Degradation as sole carbon source | | Transformation in ACSH | |
|---|---|---|---|---|
| | Transformed | Ring fission | Detected | Transformed |
| Acetosyringone | | | Y | N |
| Acetovanillone | | | Y | N |
| Benzaldehyde | $Y^1$ | | | |
| Benzoate | $Y^1$ | $Y^1$ | Y | Y |
| Benzoylformate | $Y^1$ | $Y^1$ | | |
| Caffeate | $Y^1$ | $N^1$ | | |
| Cinnamaldehyde | $Y^1$ | | | |
| Cinnamate | $Y^1$ | $Y^1$ | | |
| Coumaroyl amide | | | Y | Y |
| p-Coumaric acid | $Y^3$ | $Y^3$ | Y | Y |
| Cyclohexanecarboxylate | $Y^1$ | | | |
| A-1-cyclohexenecarboxylate | $Y^1$ | | | |
| A-3-cyclohexenecarboxylate | $Y^1$ | | | |
| Cyclohexanepropionate | $Y^1$ | | | |
| 3,4-Dihydroxybenzoic acid (protocatechuate) | $N^{1,2}$ | | Y | $Y^{**}$ |
| Ferulate | $Y^1$ | $N^1$ | Y | Y |
| Feruloyl amide | | | Y | Y |
| Hydrocaffeate | $Y^1$ | $N^1$ | | |
| Hydrocinnamaldehyde | $Y^1$ | | | |
| 4-Hydroxyacetophenone | | | Y | N |
| 4-Hydroxybenzamide | | | Y | N |
| 4-Hydroxybenzaldehyde | $Y^1$ | | Y | Y |
| 3-Hydroxybenzoate | $Y^1$ | $Y^1$ | | |
| 4-Hydroxybenzoate | $Y^1$ | $Y^1$ | Y | Y |
| 4-Hydroxybenzoylformate | $Y^1$ | $Y^1$ | | |
| 4-Hydroxycinnamate | $Y^1$ | $Y^1$ | | |
| DL-Mandelate | $Y^1$ | $Y^1$ | | |
| 4-Phenylbutyrate | $Y^1$ | $N^1$ | | |
| 3-Phenylpropionate (hydrocinnamate) | $Y^1$ | $Y^1$ | | |
| 5-Phenylvalerate | $Y^1$ | $Y^1$ | | |
| Syringaldehyde | | | Y | Y |
| Syringamide | | | Y | N |
| Syringic acid | $N^1$ | | Y | N |
| Vanillamide | | | Y | N |
| Vanillic acid | $N^1$ | | Y | N |
| Vanillin | $N^1$ | | Y | Y |

*Harwood et al. 1988 reports transformations in R. palustris CGA001, the parent strain of CGA009. Other compounds, not found in hydrolysates to date, and shown to not support anaerobic growth of R. palustris CGA001 are: 4-aminobenzoate, anthranilate (2-aminobenzoate), catechol, 3-chlorobenzoate, coniferyl alcohol, 4-cresol, cyclohexanol, cyclohexanone, ethylvanillate, 2-fluorobenzoate, gallate (trihydroxybenzoate), gentisate, nicotinate, phenol, phenoxyacetate, 3-phenylbutyrate, quinate, resorcinol, salicylate (2-hydroxybenzoate), shikimate, trimethoxybenzoate, trimethoxycinnamate, 3-toluate, 4-toluate, homogentisate, isovanillate, phenylacetate.
**Protocatechuate has been shown to be degraded if benzoic acid or p-hydroxybenzoic acid are present in the medium (Gall et al. 2013).
[1]Harwood et al. 1988.
[2]Gall et al. 2013.
[3]Pan et al. 2008.

Figure 5:
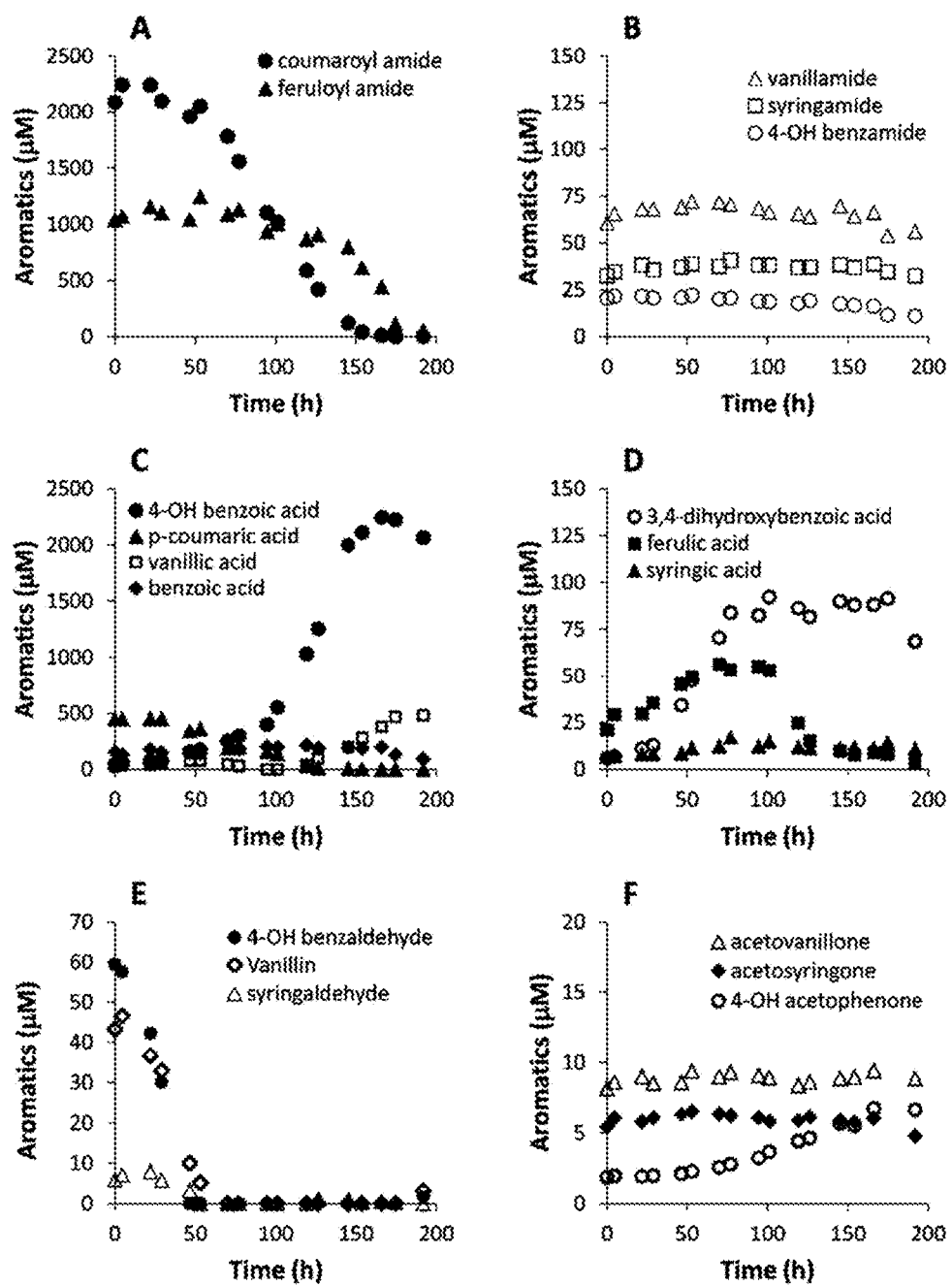
FIG. 5 shows transformation of aromatic compounds during culturing of *R. palustris* CGA009 in ACSH. The aromatic compounds include aromatic amides present at (A) high and (B) low concentrations; aromatic acids at (C) high and (D) low concentrations; (E) aromatic aldehydes; and (F) phenones.
Figure 7:
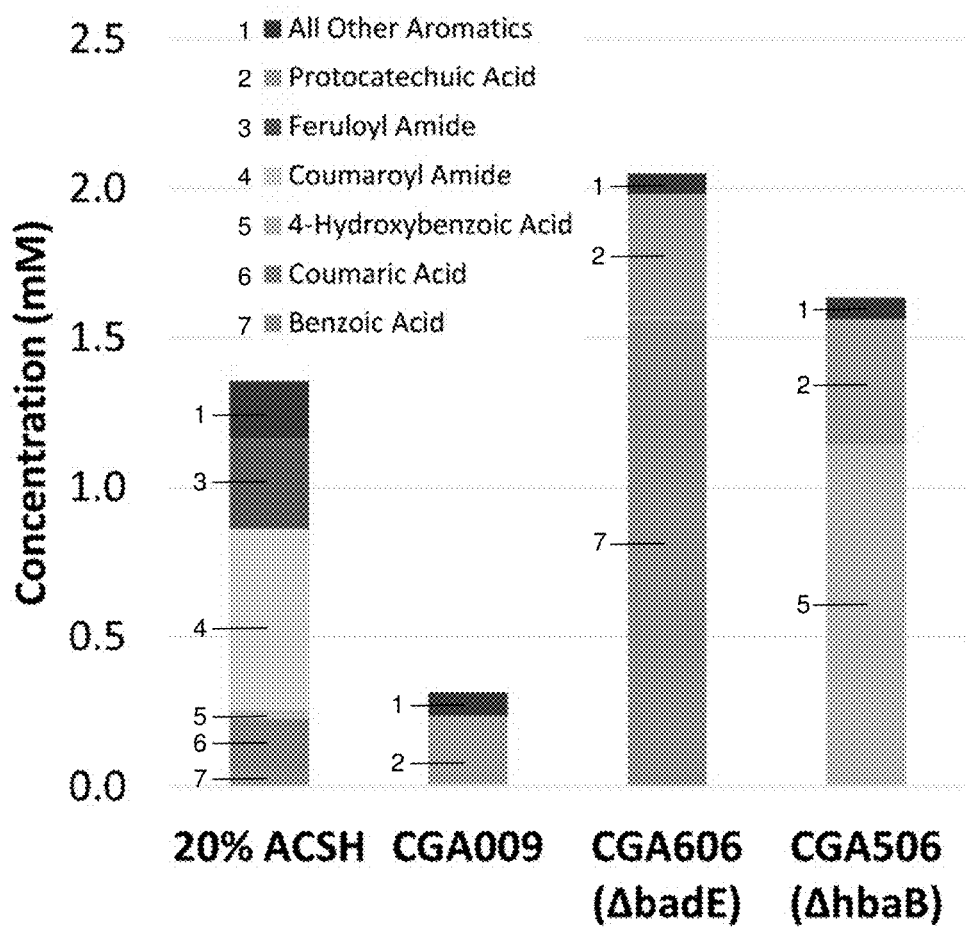
FIG. 7 shows concentrations of aromatic compounds in 20% ACSH before (20% ASCH) and after growth of *R. palustris* CGA009 (wild type), CGA506 (ΔbadE) and CGA606 (ΔhbaB).

Given the knowledge gap on the ability of R. palustris CGA009 to degrade aromatic amides and phenolics with more than one ring substitution, we evaluated the extent of aromatic transformation in ACSH (FIGS. 5 and 7). Coumaroyl amide and feruloyl amide, the two aromatic amides present at the highest concentrations in ACSH (FIG. 4), were degraded (FIG. 5, panel A). Concomitant with the degradation of these aromatics, 4-hydroxybenzoic acid, vanillic acid, and 3,4-dihydroxybenzoic acid accumulated in the medium (FIG. 5, panels C and D), suggesting that these aromatics are intermediates in the degradation of the propanoyl amides. Ferulic acid transiently accumulated, but was almost completely degraded toward the end of the experiment (FIG. 5, panel D). p-Coumaric acid was also degraded (FIG. 5, panel C). In addition, aromatic benzaldehydes, present at much lower concentrations (FIG. 5, panel E) were rapidly transformed, regardless of the number of methoxy groups that they contained, while the aromatic phenones were not degraded, and a small accumulation of 4-hydroxyacetophenone was observed (FIG. 5, panel F).

This experiment demonstrated for the first time that R. palustris CGA009 has the ability to degrade coumaroyl amide and feruloyl amide, although the other three aromatic amides present in ACSH, vanillamide, syringamide, and 4-hydroxybenzamide, were not transformed (FIG. 5, panel B). Based on the knowledge of p-coumaric acid degradation (Pan et al. 2008, Phattarasukol et al. 2012), a possible route for coumaroyl amide degradation may be an initial removal of the amine group and activation to coumaroyl-CoA, followed by removal of the alkyl chain leading to p-hydroxybenzaldehyde and oxidation to p-hydroxybenzoic acid, which then enters the benzoyl-CoA pathway after CoA-ligation. Certainly, the large accumulation of p-hydroxybenzoic acid (FIG. 5, panel C) suggests that CoA ligation of p-hydroxybenzoic acid is a limiting step in this pathway. Feruloyl amide may undergo similar transformations, with the removal of the alkyl chain after CoA ligation resulting in the formation of vanillin, and then accumulation of vanillic acid. Although it has been shown that vanillic acid is not degraded by R. palustris CGA001 (Harwood et al. 1988), the parent strain of R. palustris CGA009 (CGA009 is a chloramphenicol resistant derivative of CGA001), there is evidence that other R. palustris strains can use vanillic acid as a sole carbon source (Harwood et al. 1988). In the experiment with ACSH, the molar accumulation of vanillic acid was about one half of the initial concentration of feruloyl amide (FIG. 5), suggesting that some degradation of vanillic acid occurred. In separate experiments with two-fold diluted ACSH and longer incubation times we observed complete removal of vanillic acid, and therefore, we suggest that the accumulation of vanillic acid in FIG. 5 (panel C) is reflecting a transient buildup of this metabolite. In support of this interpretation we note that the large accumulation of p-hydroxybenzoic acid is also transient as this compound is well known to be metabolized via the benzoyl-CoA pathway (FIG. 2) (Gibson et al. 1997). Likewise, the seemingly stable concentration of benzoic acid in the medium is likely due to it being actively produced and consumed during the experiment. More intriguing is the accumulation of 3,4-dihydroxybenzoic acid (protocatechuate) in the medium, since it is difficult to discern the source of this intermediate. One possibility is the removal of a methoxy group from the mono methoxylated aromatics during the degradation of vanillic acid and ferulic acid, although there is no prior knowledge that such transformation is catalyzed by R. palustris. Additional experiments with vanillic acid as the sole carbon sources showed no growth of R. palustris CGA009, while experiments with ferulic acid showed moderate growth and accumulation of vanillic acid (but not protocatechuic acid), consistent with the earlier observations with the parental strain CGA001 (Harwood et al. 1988). Another possibility is that protocatechuic acid is produced from the degradation of plant-derived aromatics present in ACSH but not yet identified. Regardless, we also anticipate that protocatechuic acid will be slowly degraded via the benzoyl-CoA pathway as demonstrated earlier (Gall et al. 2013). As a sole carbon source, *R. palustris* CGA009 cannot degrade protocatechuic acid, but this aromatic is degraded when benzoic acid or p-hydroxybenzoic acid are also present, suggesting that these compounds induce the benzoyl-CoA pathway, which does not get induced in the presence of protocatechuate alone (Gall et al. 2013). The same synergy that allows *R. palustris* to degrade protocatechuate in the presence of other aromatics may be an explanation for the observed degradation of vanillic acid in ACSH but not when supplied as a sole carbon source, as discussed above.

While these experiments extend the knowledge on the range of plant-derived aromatics that *R. palustris* CGA009 can degrade, some compounds remained unutilized in ACSH. Specifically, there is no evidence that *R. palustris* CGA009 has the ability to degrade acetophenones, or dimethoxylated aromatics other than syringaldehyde (FIG. 5).

*R. palustris* CGA009 Removes the Short Chain Organic Acids but does not Consume the Sugars Found in ACSH.

Figure 6:
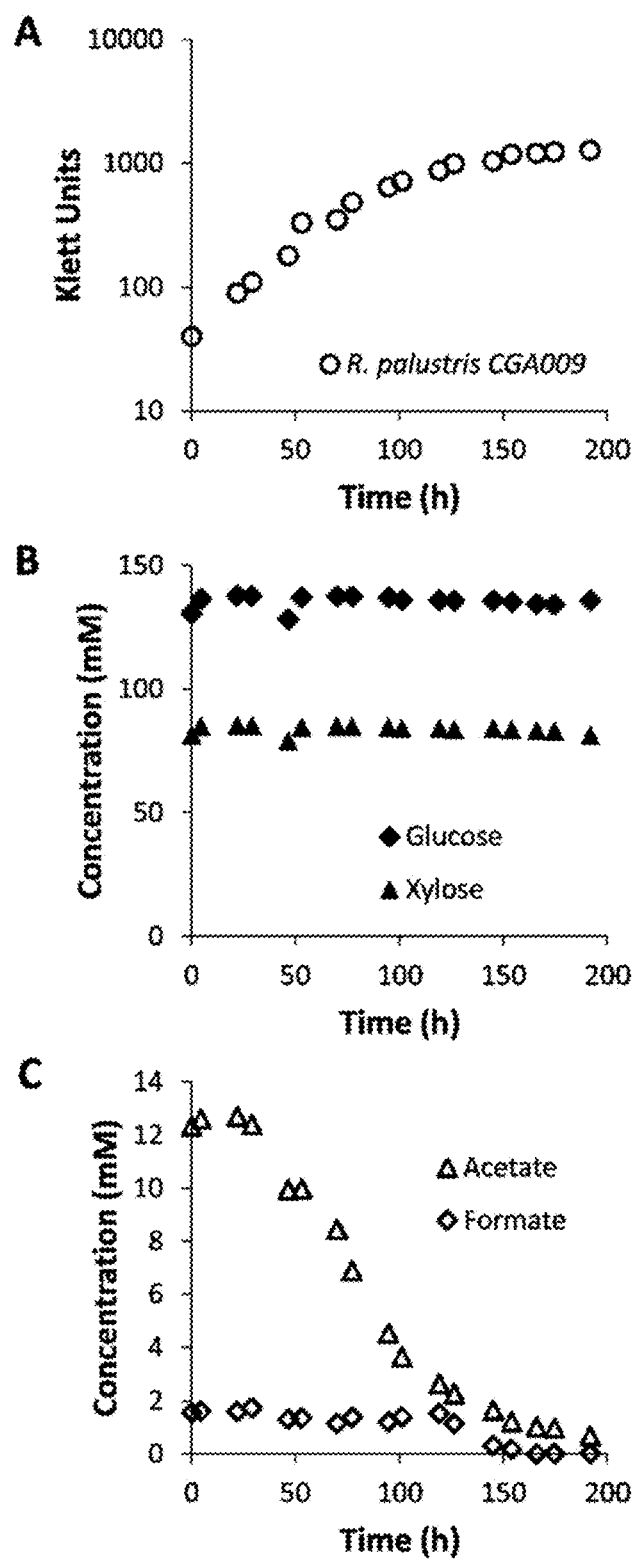
FIG. 6 shows growth (A), concentration of sugars (B), and concentration of short-chain organic acid (C) during culturing of *R. palustris* CGA009 in ACSH.

The removal of aromatic compounds and acetate from hydrolysates alleviates metabolic stress in microorganisms used for fermentative production of ethanol from cellulosic biomass hydrolysates (Delgenes et al. 1996, Keating et al. 2014, Larsson et al. 2000). An effective hydrolysate pretreatment selectively removes the inhibitors, while leaving the sugars and other essential nutrients available for downstream fermentation. As shown in FIG. 6, *R. palustris* CGA009 does not consume glucose and xylose, the main sugars present in corn stover hydrolysate. Instead, the main organic growth substrate was acetate.

Biotransformation of Aromatics with Accumulation of Benzoic Acid Using *R. palustris* Mutants.

If the most abundant aromatics present in ACSH are biotransformed via the benzoyl-CoA pathway, blocking this pathway can lead to partial transformations of some aromatics, but without ring cleavage. We showed this with *R. palustris* CGA606, a mutant with an insertion in the badE gene that inactivates benzoyl-CoA reductase (FIG. 2) and prevents de-aromatization of benzoyl-CoA (Teymouri et al. 2005). Experiments with the BadE mutant showed transformation of aromatic compounds, with a significant accumulation of benzoic acid in the medium (FIG. 7). Since benzoic acid is not present at high levels in ACSH and remained at low concentrations during the pretreatment with *R. palustris* CGA009 (FIG. 5, panel C), its accumulation when ACSH is pretreated with *R. palustris* CGA606 is a consequence of losing BadE activity (which normally uses benzoyl-CoA as a substrate). We also used *R. palustris* CGA506, which lacks 4-hydroxybenzoyl-CoA reductase (HbaBCD) activity (Gibson et al. 1997), and therefore would block degradation of para-hydroxylated aromatics but not benzoic acid. These experiments showed transformation of aromatic compounds and accumulation of 4-hydroxybenzoic acid in the medium (FIG. 7). HbaBCD uses 4-hydroxybenzoyl-CoA as a substrate (FIG. 2), so the accumulation of 4-hydroxybenzoic acid in the medium predicts that metabolism of the aromatics in ACSH also uses this enzyme. More importantly, these experiments not only show that most of the aromatics degraded are shuttled though a central pathway where the aromatic ring is reduced (FIGS. 2 and 7, CGA009), but also demonstrates the ability of engineered *R. palustris* strains to convert a diverse pool of aromatics into a single compound (such as benzoic acid or 4-hydroxybenzoic acid) (FIG. 7, CGA606 and CGA506).

Biological Removal of Aromatics from ACSH can Improve the Growth of a Second Bacterium.

The negative effect of aromatic compounds on ethanologenic fermentations has been well documented, with p-coumaric acid (Okayama et al. 1989), benzoic acid (Verduyn et al. 1992), p-hydroxybenzaldehyde (Klinke et al. 2003, Delgenes et al. 1996), vanillin (Klinke et al. 2003, Fitzgerald et al. 2004), 4-hydroxyacetophenone (Klinke et al. 2003), acetovanillone (Klinke et al. 2003), and aromatic amides (Keating et al. 2014) reported to be inhibitory to bacterial or yeast ethanologens.

Our experiments show that most of these compounds can be removed with *R. palustris* CGA009 (FIGS. 5 and 7 and Table 1), and therefore, *R. palustris*-based pretreatment can help reduce metabolic stress in ethanologenic fermentations. Beyond ethanol, the biological production of other advanced biofuels from cellulosic biomass is likely also compromised by the presence of aromatics inhibitors in hydrolysates, and therefore, their effective removal is essential to facilitate developments targeting the production of advanced biofuels and other biochemicals from hydrolysates. *Rhodobacter sphaeroides* can be used for production of advanced biofuels, such as long-chain fatty acids and furans (Lemke et al. 2014, Lemmer et al. 2015), and therefore, we used *R. sphaeroides* to evaluate the effect of pretreating ACSH with *R. palustris*.

Figure 9:
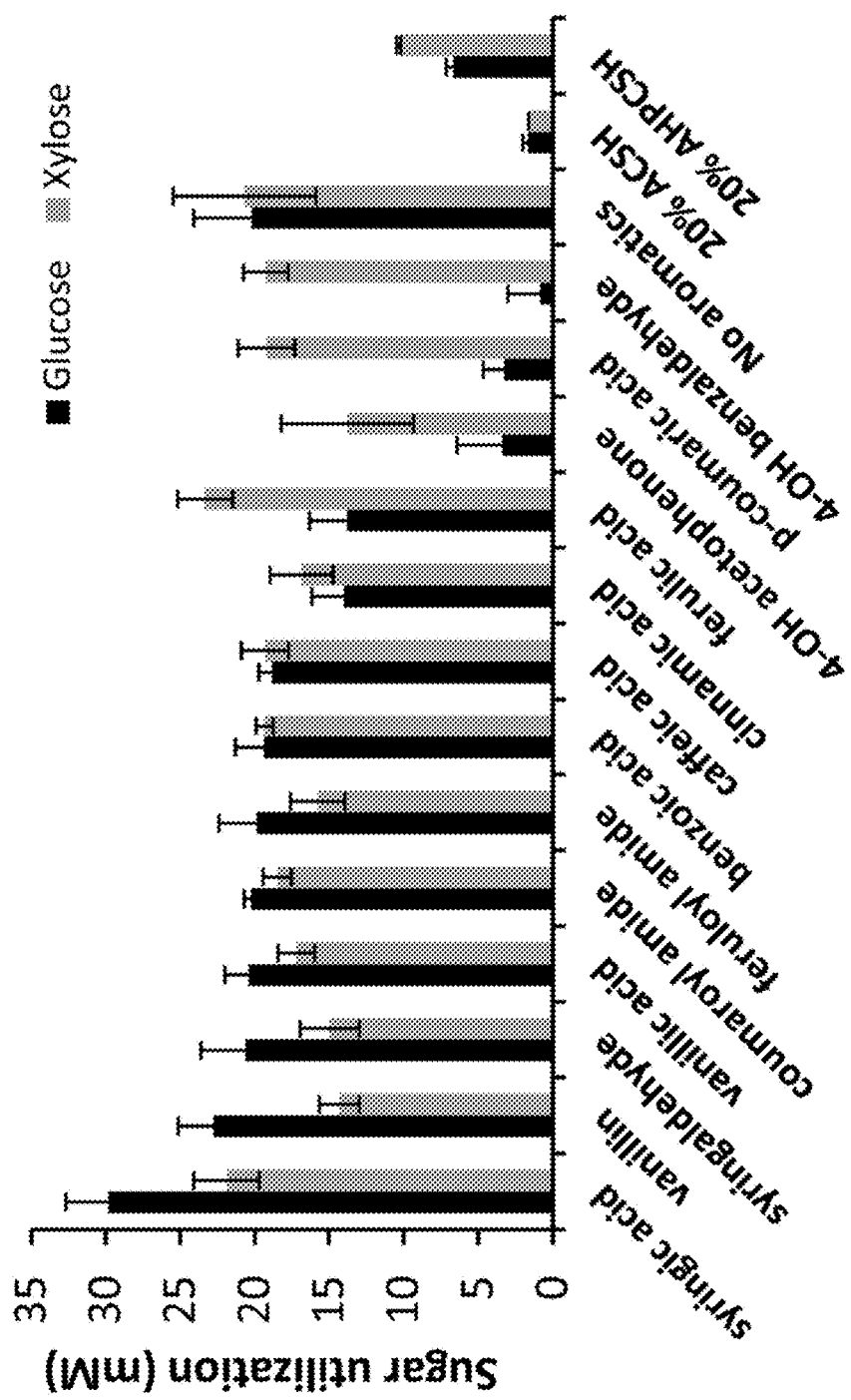
FIG. 9 shows glucose and xylose consumption by *R. sphaeroides* 2.4.1 in synthetic hydrolysate prepared by adding individual aromatics to the SynH2⁻ recipe at concentrations present in SynH2 (Keating et al. 2014), and diluting the resulting synthetic hydrolysates to 20% strength. For comparison, glucose and xylose utilization in 20% SynH2⁻ (no aromatics), as well as in 20% ACSH and 20% AHPCSH are also included.
Figure 10:
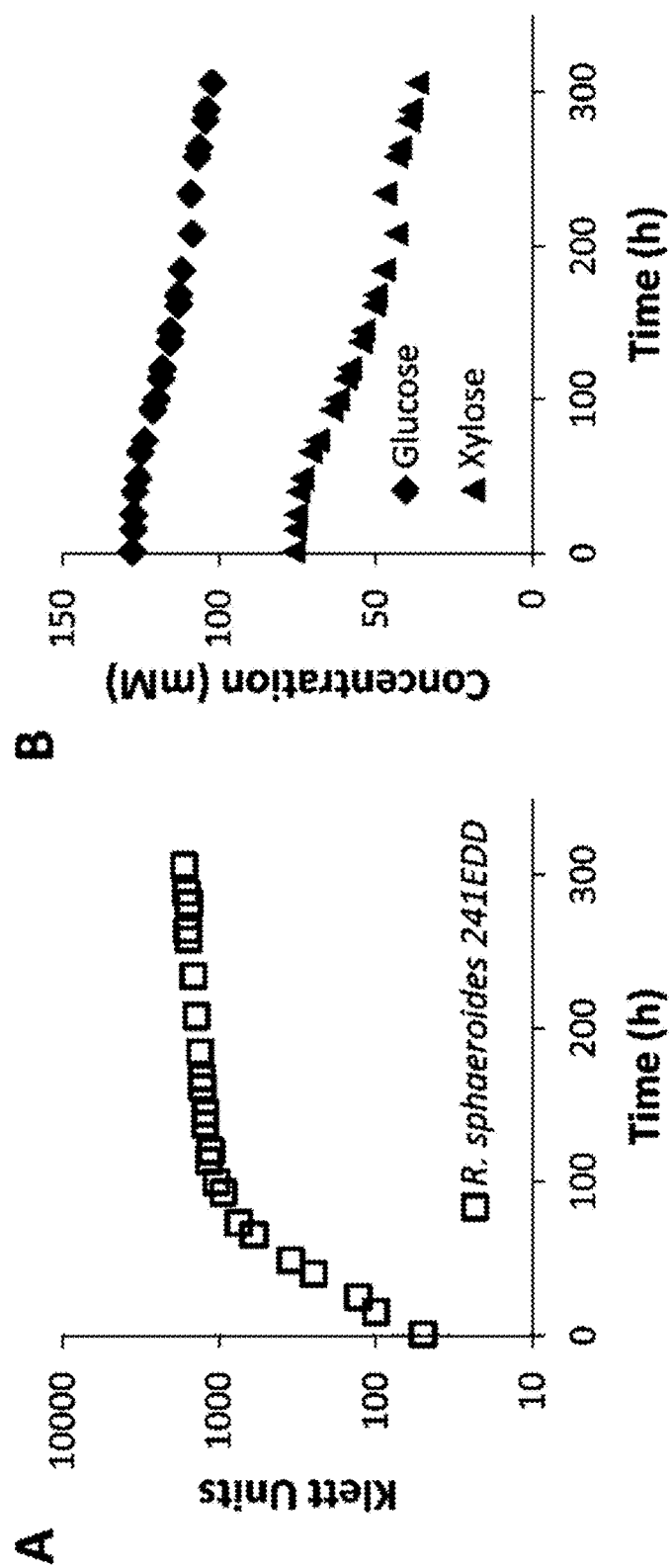
FIG. 10 shows growth of *R. sphaeroides* 241EDD (A) and sugar utilization (B) in ACSH that had been pretreated with *R. palustris* CGA009.

Although *R. sphaeroides* can be used to produce fatty acids from organic substrates (Kim et al. 2013), it does not grow at the ACSH concentrations used in this study. However, after pretreating ACSH with *R. palustris* CGA009, we filter-sterilized the spent culture medium, and then inoculated the filtered medium with *R. sphaeroides* 241EDD, a strain with an improved rate of glucose utilization. This pretreatment enabled *R. sphaeroides* to utilize the sugars, thus demonstrating the usefulness of removing inhibitory compounds during the pretreatment of the hydrolysate with *R. palustris* CGA009 (FIG. 10). From separate experiments with *R. sphaeroides* in the presence of the aromatic compounds found in ACSH, we know that p-coumaric acid, p-hydroxybenzaldehyde, and p-hydroxyacetophenone inhibited glucose utilization, while the other aromatics were not inhibitory (FIG. 9) (Austin 2013). Pretreatment with *R. palustris* effectively removed p-coumaric and p-hydroxybenzaldehyde, but not p-hydroxyacetophenone, which remained at low concentrations in the hydrolysate (FIG. 5). Thus, the removal of the most concentrated inhibitors was sufficient to allow *R. sphaeroides* growth and sugar utilization.

Implications of the Biological Removal of Aromatics from Hydrolysates.

Our results demonstrate the possibility to exploit *R. palustris* metabolism for removal of aromatic compounds from cellulosic biomass hydrolysates. A key observation is that *R. palustris* CGA009 grown in ACSH leaves the sugars unaltered and available for biofuel production by a second microbe because it preferentially uses acetate and aromatics as electron donors. While demonstrated in this study using ACSH, removal of inhibitory aromatics with *R. palustris* could be generalized to other biomass pretreatments, such as alkaline hydrolysis, dilute-acid hydrolysis, steam explosion, and others (Kumar et al. 2009) that also generate substantial acetate and aromatics in the hydrolysates (Piotrowski et al. 2014). To achieve the full potential of this process, strains capable of growing in higher strength hydrolysates, and possibly extending the range of plant-derived aromatics that can be removed, are employed. Moreover, by engineering strains capable of channeling the transformation of aromatics into specific phenolic compounds, as demonstrated here with an *R. palustris* mutant strain that concentrated the aromatic moieties as benzoic acid, it is possible to achieve not only removal of inhibitors, but also collection and recovery of valuable chemicals from the hydrolysates. The accumulation of well-defined phenolic compounds by engineered strains of *R. palustris* adds to the diversity of biochemicals that could be recovered from a biorefinery (Ragauskas et al. 2006), and contributes to increasing the fraction of the carbon present in the hydrolysates that is recovered as a valuable product instead of being released as organic waste.

Example 2

Summary

The processing of lignocellulosic biomass typically involves extracting lignin from the biomass. This extraction typically occurs at the pretreatment stage prior to hydrolyzing the cellulose but may also or alternatively occur after hydrolysis. Regardless of the order of steps, the lignin extraction generally results in a fraction highly enriched in lignin aromatics with minimal amounts of sugars. Example 1 showed that *R. palustris* can grow on diluted lignocellulosic biomass hydrolysate and can either degrade or transform the plant-derived aromatics from the hydrolysate for downstream processing or chemical upgrading. The present example shows that *R. palustris* can also grow on lignin extracts as sole carbon substrate and, as with the hydrolysate, can either degrade or transform the aromatics for downstream processing or chemical upgrading.

Methods

Crude lignin extract was obtained by extractive ammonia (EA) pretreatment as described in da Costa Sousa et al. 2016. This process creates several product streams, and here, the ammonia-soluble lignin fraction was used. EA extracted lignin has been reported to contain 44% of the lignin present in the original biomass, while only extracting less than 5% of the carbohydrates present (da Costa Sousa et al. 2016). This ammonia soluble crude lignin extract therefore contains a variety of organic compounds including water-soluble aromatic compounds and water-insoluble aromatic compounds (da Costa Sousa et al. 2016).

Ammonia was removed from the crude EA lignin extract. The extract was then mixed with water and adjusted to pH 5. After mixing thoroughly, the solution was filtered to remove the non-water soluble fraction of the EA-extracted lignin. The aromatics were extracted from the water with ethyl acetate (EtOAc) by mixing the water with the EtOAc, partitioning the water and the EtOAc in immiscible layers, and recovering the EtOAc. The EtOAc was evaporated, resulting in a dry, aromatic-containing resin.

The EtOAc-extracted resin, which contained only the fraction of EA-extracted lignin that was both soluble in water and then partitioned to ethyl acetate, was dissolved in water with the pH adjusted to increase solubility. Chemical oxygen demand (COD) measurements were performed to determine the amount of organic compounds contained in the water, and an appropriate amount of the aromatic-containing water was added to photosynthetic medium (PM) prepared as described in (Kim et al. 1991). The PM was devoid of sugars or organic substrate other than the organics provided by the EtOAc-extracted resin. *R. palustris* strains CGA009, CGA606, and CGA506 were grown in the aromatic-containing PM under anaerobic conditions as described above in Example 1.

Results and Discussion

Growth of *R. palustris* on EtOAc-Extracted Resin, Derived from the Water Soluble Fraction of EA-Lignin.

Figure 8:
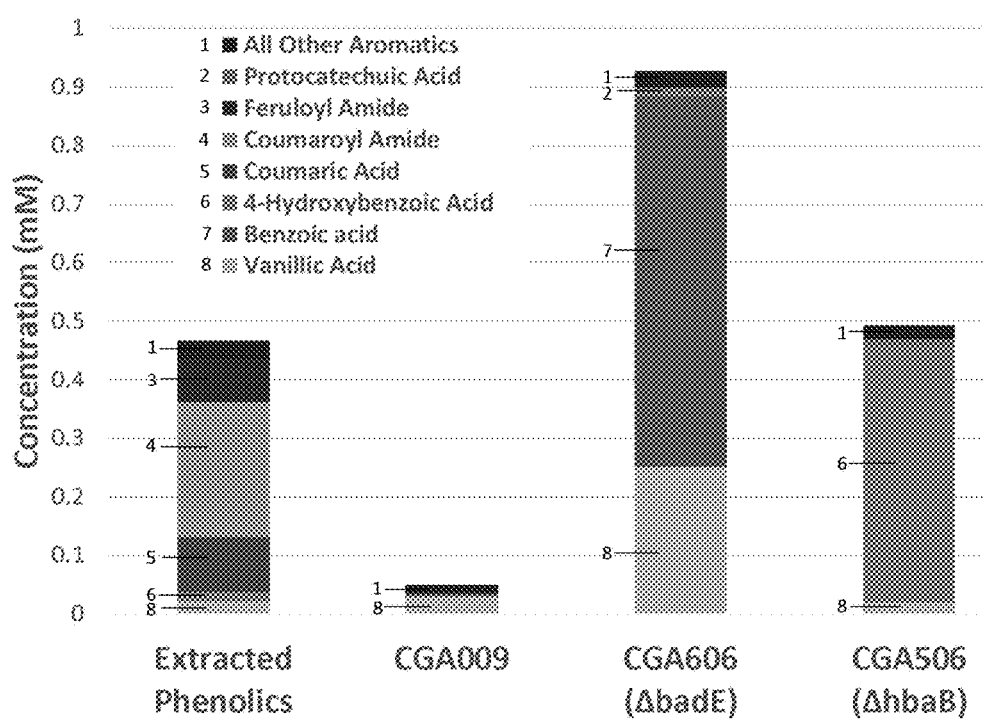
FIG. 8 shows concentrations of aromatic compounds in lignin extract before (Extracted Phenolics) and after growth of *R. palustris* CGA009 (wild type), CGA606 (ΔbadE), and CGA506 (ΔhbaB).

The ability of *R. palustris* strains CGA009, CGA606 (ΔbadE), and CGA506 (ΔhbaB) to grow on media made from EtOAc-extracted resin and to degrade or transform the aromatics therein was assessed. FIG. 8 shows the lignin aromatics present in the media before and after growth of *R. palustris* strains CGA009, CGA606, and CGA506.

The lignin aromatics present in the EtOAc-extracted resin before growth of *R. palustris* showed high concentrations of feruloyl amide, coumaroyl amide, and coumaric acid and much lower amounts of 4-hydroxybenzoic acid, benzoic acid, vanillic acid, and other aromatics. Growth of *R. palustris* CGA009 on the EtOAc-extracted resin resulted in consumption of nearly all of the feruloyl amide, coumaroyl amide, coumaric acid, and 4-hydroxybenzoic acid. Growth of *R. palustris* CGA606 on the EtOAc-extracted resin resulted in consumption of nearly all of the feruloyl amide, coumaroyl amide, coumaric acid, and 4-hydroxybenzoic acid and production of benzoic acid and vanillic acid. Growth of *R. palustris* CGA506 on the EtOAc-extracted resin resulted in consumption of nearly all of the feruloyl amide, coumaroyl amide, and coumaric acid and production of 4-hydroxybenzoic acid.

These results show that *R. palustris* can grow on EtOAc-extracted lignin products containing ethyl acetate-extracted, water-soluble aromatic compounds derived from EA-extracted lignin as the sole carbon substrate and can degrade or transform the aromatics therein for downstream processing or chemical upgrading. We predict the same activity of *R. palustris* and other microorganisms disclosed herein on other lignin extracts.

CITED REFERENCES

Alonso M V, Oliet M, Rodriguez F, Garcia J, Gilarranz M A and Rodriguez J J, *Bioresour. Technol.*, 2005, 96, 1013-1018.

Anders H J, Kaetzke A, Kampfer P, Ludwig W, Fuchs G. Taxonomic position of aromatic-degrading denitrifying pseudomonad strains K 172 and K B 740 and their description as new members of the genera *Thauera*, as *Thauera aromatica* sp. nov., and *Azoarcus*, as *Azoarcus evansii* sp. nov., respectively, members of the beta subclass of the Proteobacteria. *Int J Syst Bacteriol.* 1995 April; 45(2):327-33.

Auburger G, Winter J. Activation and degradation of benzoate, 3-phenylpropionate and crotonate by *Syntrophus buswellii* strain G A. Evidence for electron-transport phosphorylation during crotonate respiration. *Appl Microbiol Biotechnol.* 1996 February; 44(6):807-15.

Austin, S. Utilization of corn stover hydrolysates by *Rhodobacter sphaeroides* and *Rhodopseudomonas palustris* under photoheterotrophic conditions. M S Thesis, University of Wisconsin, Madison, 2013.

Bak, F. and Widdel, F. (1986) Anaerobic degradation of phenol and phenol derivatives by *Desulfobacterium phenolicum* gen. nov., sp. nov. *Arch. Microbiol.* 1986 146: 177-180.

Barbosa, M. J.; Rocha, J. M. S.; Tramper, J.; Wijffels, R. H., Acetate as a carbon source for hydrogen production by photosynthetic bacteria. *J. Biotechnol.* 2001, 85, (1), 25-33.

Beller H R, Spormann A M, Sharma P K, Cole J R, Reinhard M. Isolation and characterization of a novel toluene-degrading, sulfate-reducing bacterium. *Appl Environ Microbiol.* 1996 April; 62(4):1188-96.

Bellissimi, E.; van Dijken, J. P.; Pronk, J. T.; van Maris, A. J. A., Effects of acetic acid on the kinetics of xylose fermentation by an engineered, xylose-isomerase-based *Saccharomyces cerevisiae* strain. *FEMS Yeast Res.* 2009, 9, (3), 358-364.

Blake C K, Hegeman G D. Plasmid pCB1 carries genes for anaerobic benzoate catabolism in *Alcaligenes xylosoxidans* subsp. *denitrificans* PN-1. *J Bacteriol.* 1987 November; 169(11):4878-83.

Breese K, Boll M, Alt-Mörbe J, Schägger H, Fuchs G. Genes coding for the benzoyl-CoA pathway of anaerobic aromatic metabolism in the bacterium *Thauera aromatica*. *Eur J Biochem.* 1998 Aug. 15; 256(1):148-54.

Chambel, A.; Viegas, C. A.; Sa-Correia, I., Effect of cinnamic acid on the growth and on plasma membrane H+-ATPase activity of *Saccharomyces cerevisiae*. *Int. J. Food Microbiol.* 1999, 50, (3), 173-179.

Chundawat S P S, Vismeh R, Sharma L N, Humpula J F, da Costa Sousa L, Chambliss C K, Jones A D, Balan V and Dale B E, Bioresour. Technol., 2010, 101, 8429-8438.

Chundawat S P S, Donohoe B S, Sousa L D, Elder T, Agarwal U. P, Lu F C, Ralph J, Himmel M. E, Balan V, and Dale B E, *Energy Environ. Sci.,* 2011, 4, 973-984.

da Costa Sousa, L.; Leonardo, Jin, M.; Chundawat, S. P. S.; Bokade, V.; Tang, X.; Azarpira, A.; Lu, F.; Avci, F.; Humpula, J.; Uppugundla, N.; Gunawan, C.; Pattathil, S.; Cheh, A. M.; Kothari, N.; Kumar, N.; Ralph, J.; Hahn, M. G.; Wyman, C. E.; Singh, S.; Simmons, B. A.; Dale, B. E.; Balan, V. Next-Generation Ammonia Pretreatment Enhances Cellulosic Biofuel Production. *Energy Environ. Sci.,* 2016, 9, 1215-1223.

Delgenes, J. P.; Moletta, R.; Navarro, J. M., Effects of lignocellulose degradation products on ethanol fermentations of glucose and xylose by *Saccharomyces cerevisiae, Zymomonas mobilis, Pichia stipitis,* and *Candida shehatae*. *Enzyme Microb. Technol.* 1996, 19, (3), 220-225.

Dutton, P. L.; Evans, W. C., The Metabolism of Aromatic Compounds by *Rhodopseudomonas palustris*. *Biochem. J.* 1969, 113, 525.

Egland, P. G.; Pelletier, D. A.; Dispensa, M.; Gibson, J.; Harwood, C. S., A cluster of bacterial genes for anaerobic benzene ring biodegradation. *Proc. Natl. Acad. Sci. USA* 1997, 94, (12), 6484-6489.

Fitzgerald, D. J.; Stratford, M.; Gasson, M. J.; Ueckert, J.; Bos, A.; Narbad, A., Mode of antimicrobial action of vanillin against *Escherichia coli, Lactobacillus plantarum* and *Listeria innocua*. *J. Appl. Microbiol.* 2004, 97, (1), 104-113.

Gall, D. L.; Ralph, J.; Donohue, T. J.; Noguera, D. R., Benzoyl coenzyme A pathway-mediated metabolism of meta-hydroxy-aromatic acids in *Rhodopseudomonas palustris*. *J Bacteriol* 2013, 195, (18), 4112-20.

Gibson, J.; Dispensa, M.; Harwood, C. S., 4-hydroxybenzoyl coenzyme A reductase (dehydroxylating) is required for anaerobic degradation of 4-hydroxybenzoate by *Rhodopseudomonas palustris* and shares features with molybdenum-containing hydroxylases. *J. Bacteriol.* 1997, 179, (3), 634-642.

Gorny N, Schink B. Anaerobic degradation of catechol by *Desulfobacterium* sp. strain Cat2 proceeds via carboxylation to protocatechuate. *Appl Environ Microbiol.* 1994 September; 60(9):3396-400.

Harrison, F. H.; Harwood, C. S., The pimFABCDE operon from *Rhodopseudomonas palustris* mediates dicarboxylic acid degradation and participates in anaerobic benzoate degradation. *Microbiology-Sgm* 2005, 151, 727-736.

Harwood, C. S.; Gibson, J., Anaerobic and aerobic metabolism of diverse aromatic compounds by the photosynthetic bacterium *Rhodopseudomonas palustris*. *Appl. Environ. Microbiol.* 1988, 54, (3), 712-717.

Harwood, C. S.; Burchhardt, G.; Herrmann, H.; Fuchs, G., Anaerobic metabolism of aromatic compounds via the benzoyl-CoA pathway. *FEMS Microbiol. Rev.* 1998, 22, (5), 439-458.

Hirakawa, H.; Schaefer, A. L.; Greenberg, E. P.; Harwood, C. S., Anaerobic p-Coumarate Degradation by *Rhodopseudomonas palustris* and Identification of CouR, a MarR Repressor Protein That Binds p-Coumaroyl Coenzyme A. *J. Bacteriol.* 2012, 194, (8), 1960-1967.

Hopkins B T, McInerney M J, Warikoo V. Evidence for anaerobic syntrophic benzoate degradation threshold and isolation of the syntrophic benzoate degrader. *Appl Environ Microbiol.* 1995 February; 61(2):526-30.

Humpula, J. F.; Chundawat, S. P. S.; Vismeh, R.; Jones, A. D.; Balan, V.; Dale, B. E., Rapid quantification of major reaction products formed during thermochemical pretreatment of lignocellulosic biomass using G C-M S. *Journal of Chromatography B-Analytical Technologies in the Biomedical and Life Sciences* 2011, 879, (13-14), 1018-1022.

Iwaki, A.; Ohnuki, S.; Suga, Y.; Izawa, S.; Ohya, Y., Vanillin Inhibits Translation and Induces Messenger Ribonucleoprotein (mRNP) Granule Formation in *Saccharomyces cerevisiae*: Application and Validation of High-Content, Image-Based Profiling. *Plos One* 2013, 8, (4).

Jonsson, L. J.; Palmqvist, E.; Nilvebrant, N. O.; Hahn-Hagerdal, B., Detoxification of wood hydrolysates with laccase and peroxidase from the white-rot fungus *Trametes versicolor*. *Appl. Microbiol. Biotechnol.* 1998, 49, (6), 691-697.

Keating, D. H.; Zhang, Y.; Ong, I. M.; McIlwain, S.; Morales, E. H.; Grass, J. A.; Tremaine, M.; Bothfeld, W.; Higbee, A.; Ulbrich, A.; Balloon, A.; Westphall, M. S.; Aldrich, J.; Lipton, M. S.; Kim, J.; Moskvin, O.; Bukhman, Y. V.; Coon, J.; Kiley, P. J.; Bates, D. M.; Landick, R., Aromatic inhibitors derived from ammonia-pretreated lignocellulose hinder bacterial ethanologenesis by activating regulatory circuits controlling inhibitor efflux and detoxification. *Frontiers in Microbiology* 2014, 5.

Kim, M. K.; Harwood, C. S., Regulation of benzoate-CoA ligase in *Rhodopseudomonas palustris*. *FEMS Microbiol. Lett.* 1991, 83, (2), 199-203.

Kim, D. H.; Lee, J. H.; Hwang, Y.; Kang, S.; Kim, M. S., Continuous cultivation of photosynthetic bacteria for fatty acid production. *Bioresour. Technol.* 2013, 148, 277-282.

Klinke, H. B.; Olsson, L.; Thomsen, A. B.; Ahring, B. K., Potential inhibitors from wet oxidation of wheat straw and their effect on ethanol production of *Saccharomyces cerevisiae*: Wet oxidation and fermentation by yeast. *Biotechnol. Bioeng.* 2003, 81, (6), 738-747.

Kontur, W. S.; Shackwitz, W.; Ivanova, N.; Martin, J.; LaButti, K.; Deshpande, S.; Tice, H.; Pennachio, C.; Sodergren, E.; Weinstock, G.; Noguera, D. R.; Donohue, T. J., Revised sequence and annotation of the *Rhodobacter sphaeroides* 2.4.1 genome. *Journal of Bacteriology* 2012, 194, 7016-7017.

Kumar, P.; Barrett, D. M.; Delwiche, M. J.; Stroeve, P., Methods for Pretreatment of Lignocellulosic Biomass for Efficient Hydrolysis and Biofuel Production. *Industrial & Engineering Chemistry Research* 2009, 48, (8), 3713-3729.

Kuever J, Kulmer J, Jannsen S, Fischer U, Blotevogel K H. Isolation and characterization of a new spore-forming sulfate-reducing bacterium growing by complete oxidation of catechol. *Arch Microbiol.* 1993; 159(3):282-8.

Larimer, F. W.; Chain, P.; Hauser, L.; Lamerdin, J.; Malfatti, S.; Do, L.; Land, M. L.; Pelletier, D. A.; Beatty, J. T.; Lang, A. S.; Tabita, F. R.; Gibson, J. L.; Hanson, T. E.; Bobst, C.; Torres, J.; Peres, C.; Harrison, F. H.; Gibson, J.; Harwood, C. S., Complete genome sequence of the metabolically versatile photosynthetic bacterium *Rhodopseudomonas palustris*. *Nat. Biotechnol.* 2004, 22, (1), 55-61.

Larsson, S.; Reimann, A.; Nilvebrant, N. O.; Jonsson, L. J., Comparison of different methods for the detoxification of lignocellulose hydrolyzates of spruce. *Appl. Biochem. Biotechnol.* 1999, 77-9, 91-103.

Larsson, S.; Quintana-Sainz, A.; Reimann, A.; Nilvebrant, N. O.; Jonsson, L. J., Influence of lignocellulose-derived aromatic compounds on oxygen-limited growth and ethanolic fermentation by *Saccharomyces cerevisiae*. *Appl Biochem Biotechnol* 2000, 84-86, 617-32.

Lau, M. W.; Dale, B. E., Cellulosic ethanol production from AFEX-treated corn stover using *Saccharomyces cerevisiae* 424A(LNH-ST). *Proc. Natl. Acad. Sci. USA* 2009, 106, (5), 1368-1373.

Lemke, R. A. S.; Peterson, A. C.; Ziegelhoffer, E. C.; Westphall, M. S.; Tjellstrom, H.; Coon, J. J.; Donohue, T. J., Synthesis and scavenging role of furan fatty acids. *Proc. Natl. Acad. Sci. USA* 2014, 111, (33), E3450-E3457.

Lemmer, K.; Dohnalkova, A.; Noguera, D. R.; Donohue, T. J., Oxygen-dependent regulation of bacterial lipid production. *J. Bacteriol.* 2015, *Online first*, (3).

Lonergan D J, Jenter H L, Coates J D, Phillips E J, Schmidt T M, Lovley D R. Phylogenetic analysis of dissimilatory Fe(III)-reducing bacteria. *J Bacteriol.* 1996 April; 178(8): 2402-8.

Lovley D R, Giovannoni S J, White D C, Champine J E, Phillips E J, Gorby Y A, Goodwin S. *Geobacter metallireducens* gen. nov. sp. nov., a microorganism capable of coupling the complete oxidation of organic compounds to the reduction of iron and other metals. *Arch Microbiol.* 1993; 159(4):336-44.

Lovley D R, Lonergan D J. Anaerobic Oxidation of Toluene, Phenol, and p-Cresol by the Dissimilatory Iron-Reducing Organism, GS-15. *Appl Environ Microbiol.* 1990 June; 56(6):1858-64.

Macala G S, Matson T D, Johnson C L, Lewis R S, Iretskii A V and Ford P C, *ChemSusChem,* 2009, 2, 215-217.

Mackenzie, C.; Choudhary, M.; Larimer, F. W.; Predki, P. F.; Stilwagen, S.; Armitage, J. P.; Barber, R. D.; Donohue, T. J.; Hosler, J. P.; Newman, J. E.; Shapleigh, J. P.; Sockett, R. E.; Zeilstra-Ryalls, J.; Kaplan, S., The home stretch, a first analysis of the nearly completed genome of *Rhodobacter sphaeroides* 2.4.1. *Photosynthesis Res.* 2001, 70, (1), 19-41.

Mountfort D O, Brulla W J, Krumholz L R, and Bryant M P. *Syntrophus buswelli* gen. nov., sp. nov.: a benzoate catabolizer from methanogenic ecosystems. *Int. J. Syst. Bacteriol.* 1984 34:216-217.

Nozawa T, Maruyama Y. Anaerobic metabolism of phthalate and other aromatic compounds by a denitrifying bacterium. *J Bacteriol.* 1988 December; 170(12):5778-84.

Okayama, H.; Curiel, D. T.; Brantly, M. L.; Holmes, M. D.; Crystal, R. G., Rapid, Nonradioactive Detection of Mutations in the Human Genome by Allele-specific Amplification. *Journal of Laboratory and Clinical Medicine* 1989, 114, (2), 105-113.

Palmqvist, E.; Hahn-Hagerdal, B., Fermentation of lignocellulosic hydrolysates. I: inhibition and detoxification. *Bioresour. Technol.* 2000, 74, (1), 17-24.

Pan, C.; Oda, Y.; Lankford, P. K.; Zhang, B.; Samatova, N. F.; Pelletier, D. A.; Harwood, C. S.; Hettich, R. L., Characterization of anaerobic catabolism of p-coumarate in *Rhodopseudomonas palustris* by integrating transcriptomics and quantitative proteomics. *Mol. Cell.* Proteomics 2008, 7, (5), 938-948.

Pan X J, *J Biobased Mater Bioenergy,* 2008, 2, 25-32.

Parawira, W.; Tekere, M., Biotechnological strategies to overcome inhibitors in lignocellulose hydrolysates for ethanol production: review. *Crit. Rev. Biotechnol.* 2011, 31, (1), 20-31.

Pattathil S, Hahn M G, Dale B E and Chundawat S P S, *J. Exp. Bot.,* 2015.

Phattarasukol, S.; Radey, M. C.; Lappala, C. R.; Oda, Y.; Hirakawa, H.; Brittnacher, M. J.; Harwood, C. S., Identification of a p-Coumarate Degradation Regulon in *Rhodopseudomonas palustris* by Xpression, an Integrated Tool for Prokaryotic RNA-Seq Data Processing. *Appl. Environ. Microbiol.* 2012, 78, (19), 6812-6818.

Piotrowski, J. S.; Zhang, Y. P.; Bates, D. M.; Keating, D. H.; Sato, T. K.; Ong, I. M.; Landick, R., Death by a thousand cuts: the challenges and diverse landscape of lignocellulosic hydrolysate inhibitors. *Frontiers in Microbiology* 2014, 5.

Rabus R, Nordhaus R, Ludwig W, Widdel F. Complete oxidation of toluene under strictly anoxic conditions by a new sulfate-reducing bacterium. *Appl Environ Microbiol.* 1993 May; 59(5):1444-51.

Ragauskas, A. J.; Williams, C. K.; Davison, B. H.; Britovsek, G.; Cairney, J.; Eckert, C. A.; Frederick, W. J.; Hallett, J. P.; Leak, D. J.; Liotta, C. L.; Mielenz, J. R.; Murphy, R.; Templer, R.; Tschaplinski, T., The path forward for biofuels and biomaterials. *Science* 2006, 311, (5760), 484-489.

Ragauskas A. J., Beckham G. T., Biddy M. J., Chandra R., Chen F., Davis M. F., Davison B. H., Dixon R. A., Gilna P., Keller M., Langan P., Naskar A. K., Saddler J. N., Tschaplinski T. J., Tuskan G. A. and Wyman C. E., *Sci.,* 2014, 344.

Reknes K and Gustafsson J, *Spec. Publ.,* 2000, 195.

Rhee S K, Lee G M, Yoon J H, Park Y H, Bae H S, Lee S T. Anaerobic and aerobic degradation of pyridine by a newly isolated denitrifying bacterium. *Appl Environ Microbiol.* 1997 July; 63(7):2578-85.

Sathitsuksanoh N., Holtman K. M., Yelle D. J., Morgan T., Stavila V., Pelton J., Blanch H., Simmons B. A. and George A., *Green Chem.,* 2014, 16, 1236-1247.

Sato, T.; Liu, T.; Parreiras, L.; Williams, D.; Wohlbach, D.; Bice, B.; Ong, I.; Breuer, R.; Qin, L.; Busalacchi, D.; Deshpande, S.; Gasch, A.; Hodge, D., Harnessing Genetic Diversity in *Saccharomyces cerevisiae* for Improved Fermentation of Xylose in Hydrolysates of Alkaline Hydrogen Peroxide Pretreated Biomass *Appl Environ Microbiol* 2014, 80, (2), 540-554.

Schennen U, Braun K, Knackmuss H J. Anaerobic degradation of 2-fluorobenzoate by benzoate-degrading, denitrifying bacteria. *J Bacteriol.* 1985 January; 161(1):321-5.

Schnell S, Bak F, Pfennig N. Anaerobic degradation of aniline and dihydroxybenzenes by newly isolated sulfate-reducing bacteria and description of *Desulfobacterium anilini*. *Arch Microbiol*. 1989; 152(6):556-63.

Schoëcke, L. (1997) Energetik des methanogenen Benzoatabbaus durch *Syntrophus gentianae*. Thesis, University of Konstanz.

Schoëcke L and Schink B. Energetics of methanogenic benzoate degradation by *Syntrophus gentianae* in syntrophic coculture. *Microbiology* 1997 143:2345-2351.

Schuerch C. *J. Ind. Eng. Chem.*, 1963, 55, 39.

Schwalbach, M. S.; Keating, D. H.; Tremaine, M.; Marner, W. D.; Zhang, Y. P.; Bothfeld, W.; Higbee, A.; Grass, J. A.; Cotten, C.; Reed, J. L.; Sousa, L. D.; Jin, M. J.; Balan, V.; Ellinger, J.; Dale, B.; Kiley, P. J.; Landick, R., Complex Physiology and Compound Stress Responses during Fermentation of Alkali-Pretreated Corn Stover Hydrolysate by an *Escherichia coli* Ethanologen. *Appl. Environ. Microbiol*. 2012, 78, (9), 3442-3457.

Sistrom, W. R., The kinetics of the synthesis of photopigments in *Rhodopseudomonas spheroides*. *J Gen Microbiol* 1962, 28, 607-16.

Song B, Young L Y, Palleroni N J. Identification of denitrifier strain T1 as *Thauera aromatica* and proposal for emendation of the genus *Thauera* definition. *Int J Syst Bacteriol*. 1998 July; 48 Pt 3:889-94.

Springer N, Ludwig W, Philipp B, Schink B. *Azoarcus anaerobius* sp. nov., a resorcinol-degrading, strictly anaerobic, denitrifying bacterium. *Int J Syst Bacteriol*. 1998 July; 48 Pt 3:953-6.

Swinnen, S.; Fernandez-Nino, M.; Gonzalez-Ramos, D.; van Maris, A. J. A.; Nevoigt, E., The fraction of cells that resume growth after acetic acid addition is a strain-dependent parameter of acetic acid tolerance in *Saccharomyces cerevisiae*. *FEMS Yeast Res*. 2014, 14, (4), 642-653.

Szewzyk U and Pfennig N. Complete oxidation of catechol by the strictly anaerobic sulfate-reducing *Desulfobacterium catecholicum* sp. nov. *Arch. Microbiol*. 1987 147: 163-168.

Teymouri, F.; Laureano-Perez, L.; Alizadeh, H.; Dale, B. E., Optimization of the ammonia fiber explosion (AFEX) treatment parameters for enzymatic hydrolysis of corn stover. *Bioresour. Technol*. 2005, 96, (18), 2014-2018.

The 110th Congress of the United States, Energy Independence and Security Act of 2007. *Public Law* 110-140. In 2007.

Trajano H, Engle N, Foston M, Ragauskas A, Tschaplinski T and Wyman C, *Biotechnol. Biofuels*, 2013, 6, 110.

U.S. Environmental Protection Agency 2014 RFS2 Data, http://epa.gov/otaq/fuels/rfsdata/2014emts.htm.

U.S. DOE *Lignocellulosic biomass for advanced biofuels and bioproducts: Workshop Report, DOE/SC*-0000; U.S. Department of Energy Office of Science: Washington D.C., 2014, http://genomicscience.energy.gov/biofuels/lignocellulose/.

USEIA, *International Energy Outlook* 2011. 2011.

van Schie P M, Young L Y. Isolation and characterization of phenol-degrading denitrifying bacteria. *Appl Environ Microbiol*. 1998 July; 64(7):2432-8.

Verduyn C, Postma E, Scheffers W A, Van Dijken J P. Effect of benzoic acid on metabolic fluxes in yeasts: a continuous-culture study on the regulation of respiration and alcoholic fermentation. *Yeast*. 1992 July; 8(7):501-17.

Warikoo V, McInerney M J, Robinson J A, Suflita J M. Interspecies acetate transfer influences the extent of anaerobic benzoate degradation by syntrophic consortia. *Appl Environ Microbiol*. 1996 January; 62(1):26-32.

Widdel F and Bak F. Gram-negative mesophilic sulfate-reducing bacteria. (1992) In: The Prokaryotes (Balows, A., Trueper, H. G., Dworkin, M., Harder, W. and Schleifer, K.-H., Eds.), pp. 3352-3378. Springer, New York, N.Y.

Zakzeski J, Bruijnincx P C A, Jongerius A L and Weckhuysen B M, *Chem. Rev.*, 2010, 110, 3552-3599.

Zaldivar, J.; Martinez, A.; Ingram, L. O., Effect of selected aldehydes on the growth and fermentation of ethanologenic *Escherichia coli*. *Biotechnol Bioeng* 1999, 65, (1), 24-33.

Zhou J, Fries M R, Chee-Sanford J C, Tiedje J M. Phylogenetic analyses of a new group of denitrifiers capable of anaerobic growth of toluene and description of *Azoarcus tolulyticus* sp. nov. Int J Syst Bacteriol. 1995 July; 45(3): 500-6.

We claim:

1. A method of processing a solution comprising one or more aromatic compounds, the method comprising:
culturing a first microorganism capable of metabolizing the one or more aromatic compounds in the solution for a time sufficient to reduce an amount of the one or more aromatic compounds and thereby generate a processed solution; and
culturing a second microorganism in the processed solution, wherein:
the solution comprises pretreated lignocellulosic biomass, lignocellulosic biomass hydrolysate, or lignocellulosic biomass lignin extract;
each of the one or more aromatic compounds comprises an aromatic ring with at least one of an aldehyde moiety, an amide moiety, a carboxylate moiety, and an alcohol moiety bound directly thereto or bound thereto via an alkylene, alkenylene, or alkynylene group;
the first microorganism is a member of a genus selected from the group consisting of *Rhodopseudomonas*, *Thauera*, and *Azoarcus*, and comprises a benzoyl-CoA pathway enzyme selected from the group consisting of a 4-hydroxybenzoate-CoA ligase (EC 6.2.1.27), a benzoate-CoA ligase (EC 6.2.1.25), a 3-hydroxybenzoate-CoA ligase (EC 6.2.1.37), a 4-hydroxybenzoyl-CoA reductase (EC 1.3.7.9), and a benzoyl-CoA reductase (EC 1.3.7.8);
the second microorganism is an ethanologen or *Rhodobacter sphaeroides*; and
the culturing of the first microorganism reduces the one or more aromatic compounds by an amount effective to result in enhanced growth of the second microorganism in the processed solution compared to growth of the second microorganism in the solution without the culturing of the first microorganism.

2. The method of claim 1 wherein the aromatic ring in at least one of the one or more aromatic compounds comprises at least one of an aldehyde moiety, an amide moiety, and a carboxylate moiety bound directly thereto or bound thereto via an alkylene, alkenylene, or alkynylene group.

3. The method of claim 1 wherein the aromatic ring in at least one of the one or more aromatic compounds comprises an amide moiety bound thereto via an alkylene, alkenylene, or alkynylene group.

4. The method of claim 1 wherein the aromatic ring in at least one of the one or more aromatic compounds further comprises at least one alkoxy group bound directly thereto.

5. The method of claim 1 wherein the aromatic ring in at least one of the one or more aromatic compounds further comprises at least two alkoxy groups bound directly thereto.

6. The method of claim 1 wherein the aromatic ring in at least one of the one or more aromatic compounds comprises at least one of an aldehyde moiety and an amide moiety bound directly to the aromatic ring or bound to the aromatic ring via an alkylene, alkenylene, or alkynylene group and further comprises at least one alkoxy group bound directly thereto.

7. The method of claim 1 wherein the one or more aromatic compounds comprises p-coumaroyl amide, feruloyl amide, vanillin, syringaldehyde, or a combination thereof.

8. The method of claim 1 wherein the one or more aromatic compounds comprises at least three structurally different aromatic compounds comprising an aromatic ring with at least one of an aldehyde moiety, an amide moiety, a carboxylate moiety, and an alcohol moiety bound directly thereto or bound thereto via an alkylene, alkenylene, or alkynylene group.

9. The method of claim 1 wherein the solution comprises a lignocellulosic biomass hydrolysate.

10. The method of claim 1 wherein the solution comprises a lignocellulosic biomass lignin extract.

11. The method of claim 1 wherein the culturing of the first microorganism comprises culturing under anaerobic conditions.

12. The method of claim 1 wherein the first microorganism comprises at least one but fewer than all of a 4-hydroxybenzoate-CoA ligase (EC 6.2.1.27), a benzoate-CoA ligase (EC 6.2.1.25), a 3-hydroxybenzoate-CoA ligase (EC 6.2.1.37), a 4-hydroxybenzoyl-CoA reductase (EC 1.3.7.9), and a benzoyl-CoA reductase (EC 1.3.7.8).

13. The method of claim 12 wherein an amount of an aromatic compound increases during the time.

14. The method of claim 1 wherein the first microorganism comprises at least one of a 4-hydroxybenzoate-CoA ligase (EC 6.2.1.27), a benzoate-CoA ligase (EC 6.2.1.25), and a 3-hydroxybenzoate-CoA ligase (EC 6.2.1.37), and lacks a benzoyl-CoA reductase (EC 1.3.7.8).

15. The method of claim 14 wherein an amount of benzoic acid increases during the time.

16. The method of claim 1 wherein the first microorganism comprises at least one of a 4-hydroxybenzoate-CoA ligase (EC 6.2.1.27), a benzoate-CoA ligase (EC 6.2.1.25), and a 3-hydroxybenzoate-CoA ligase (EC 6.2.1.37), and lacks a 4-hydroxybenzoyl-CoA reductase (EC 1.3.7.9).

17. The method of claim 16 wherein an amount of 4-hydroxybenzoyl-CoA increases during the time.

18. The method of claim 1 wherein the culturing of the first microorganism reduces the one or more aromatic compounds by at least 20% by mass.

19. The method of claim 1 wherein the solution further comprises fermentable sugar and wherein the culturing of the first microorganism does not reduce the fermentable sugar or reduces the fermentable sugar by no more than 20% by mass.

20. The method of claim 1 wherein, in the absence of the first microorganism, the growth of the second microorganism is inhibited by the one or more aromatic compounds in the culture medium.

21. The method of claim 1 wherein the processed solution comprises a fermentable sugar and the second microorganism consumes the fermentable sugar during the culturing of the second microorganism.

22. The method of claim 1 wherein greater than 80% by mass of total fermentable sugar in the solution and the processed solution throughout the culturing of the first microorganism and the culturing of the second microorganism is provided by the pretreated lignocellulosic biomass, lignocellulosic biomass lignin extract, or lignocellulosic biomass hydrolysate.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Upstream edd primer

<400> SEQUENCE: 1
cgataagctt cgagctcaca ttgacg                                      26

<210> SEQ ID NO 2
<211> LENGTH: 28
<212> TYPE: DNA
<213> ORGANISM: Artificial Sequence
<220> FEATURE:
<223> OTHER INFORMATION: Downstream edd primer

<400> SEQUENCE: 2
gtacatctct agatcggctg cgctgaag                                    28